US011083790B2

(12) United States Patent
Farsaci

(10) Patent No.: US 11,083,790 B2
(45) Date of Patent: Aug. 10, 2021

(54) TREATMENT OF HODGKIN LYMPHOMA USING AN ANTI-PD-1 ANTIBODY

(71) Applicant: Bristol-Myers Squibb Company, Princeton, NJ (US)

(72) Inventor: Benedetto Farsaci, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 126 days.

(21) Appl. No.: 16/306,285

(22) PCT Filed: Jun. 1, 2017

(86) PCT No.: PCT/US2017/035492
§ 371 (c)(1),
(2) Date: Nov. 30, 2018

(87) PCT Pub. No.: WO2017/210453
PCT Pub. Date: Dec. 7, 2017

(65) Prior Publication Data
US 2019/0290757 A1 Sep. 26, 2019

Related U.S. Application Data

(60) Provisional application No. 62/344,880, filed on Jun. 2, 2016.

(51) Int. Cl.
| | | |
|---|---|---|
| A61K 39/395 | (2006.01) | |
| C07K 16/28 | (2006.01) | |
| A61P 35/00 | (2006.01) | |
| A61K 31/351 | (2006.01) | |
| A61K 31/475 | (2006.01) | |
| A61K 31/655 | (2006.01) | |
| A61K 39/00 | (2006.01) | |
| A61K 45/06 | (2006.01) | |

(52) U.S. Cl.
CPC ........ *A61K 39/3955* (2013.01); *A61K 31/351* (2013.01); *A61K 31/475* (2013.01); *A61K 31/655* (2013.01); *A61K 39/39558* (2013.01); *A61P 35/00* (2018.01); *C07K 16/28* (2013.01); *C07K 16/2818* (2013.01); *A61K 45/06* (2013.01); *A61K 2039/505* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,977,318 | A | 11/1999 | Linsley et al. |
| 6,051,227 | A | 4/2000 | Allison et al. |
| 6,682,736 | B1 | 1/2004 | Hanson et al. |
| 6,808,710 | B1 | 10/2004 | Wood et al. |
| 6,984,720 | B1 | 1/2006 | Korman et al. |
| 7,034,121 | B2 | 4/2006 | Carreno et al. |
| 7,488,802 | B2 | 2/2009 | Collins et al. |
| 7,595,048 | B2 | 9/2009 | Honjo et al. |
| 7,605,238 | B2 | 10/2009 | Korman et al. |
| 7,943,743 | B2 | 5/2011 | Korman et al. |
| 8,008,449 | B2 | 8/2011 | Korman et al. |
| 8,168,179 | B2 | 5/2012 | Honjo et al. |
| 8,168,757 | B2 | 5/2012 | Finnefrock et al. |
| 8,217,149 | B2 | 7/2012 | Irving et al. |
| 8,354,509 | B2 | 1/2013 | Carven et al. |
| 8,609,089 | B2 | 12/2013 | Langermann et al. |
| 8,728,474 | B2 | 5/2014 | Honjo et al. |
| 8,779,105 | B2 | 7/2014 | Korman et al. |
| 8,779,108 | B2 | 7/2014 | Queva et al. |
| 8,900,587 | B2 | 12/2014 | Carven et al. |
| 9,067,999 | B1 | 6/2015 | Honjo et al. |
| 9,073,994 | B2 | 7/2015 | Honjo et al. |
| 9,084,776 | B2 | 7/2015 | Korman et al. |
| 9,212,224 | B2 | 12/2015 | Cogswell et al. |
| 9,358,289 | B2 | 6/2016 | Korman et al. |
| 9,387,247 | B2 | 7/2016 | Korman et al. |
| 9,393,301 | B2 | 7/2016 | Honjo et al. |
| 9,402,899 | B2 | 8/2016 | Honjo et al. |
| 9,439,962 | B2 | 9/2016 | Honjo et al. |
| 9,492,539 | B2 | 11/2016 | Korman et al. |
| 9,492,540 | B2 | 11/2016 | Korman et al. |
| 9,856,320 | B2 | 1/2018 | Cogswell et al. |
| 10,072,082 | B2 | 9/2018 | Cogswell et al. |
| 10,138,299 | B2 | 11/2018 | Cogswell et al. |
| 10,266,594 | B1 | 4/2019 | Cogswell et al. |
| 10,266,595 | B2 | 4/2019 | Cogswell et al. |

(Continued)

FOREIGN PATENT DOCUMENTS

| | | |
|---|---|---|
| WO | WO-2004004771 A1 | 1/2004 |
| WO | WO-2006121168 A1 | 11/2006 |

(Continued)

OTHER PUBLICATIONS

Sunshine et al. (2015). Current Opinion in Pharmacology. 23:32-38.*
Batty et al. (2012). Leukemia & Lymphoma. 53(5):801-806.*
Androsky, D.J., et al., "Programmed Death Ligand 1 is Expressed by Non-hodgkin Lymphomas and Inhibits the Activity of Tumor-Associated T Cells," Clinical Cancer Research 17(13):4232-4244, The Association, United States (Jul. 2011).
Ansell, S., et al., "Nivolumab in Patients (Pts) With Relapsed or Refractory Classical Hodgkin Lymphoma (R/R cHL): Clinical Outcomes From Extended Follow-up of a Phase 1 Study (CA209-039)," Blood 126(23):583 (Dec. 2015).

(Continued)

*Primary Examiner* — Christine J Saoud
*Assistant Examiner* — Jon M Lockard
(74) *Attorney, Agent, or Firm* — Sterne, Kessler, Goldstein & Fox P.L.L.C.

(57) ABSTRACT

This disclosure provides to methods for treating Hodgkin lymphoma in a subject comprising nivolumab, a PD-1-blocking antibody, that inhibits tumor immune evasion in patients with relapsed or refractory Hodgkin's lymphoma.

11 Claims, 6 Drawing Sheets

(56) References Cited

U.S. PATENT DOCUMENTS

| | | |
|---|---|---|
| 10,266,596 B1 | 4/2019 | Cogswell et al. |
| 10,308,714 B2 | 6/2019 | Cogswell et al. |
| 10,316,090 B2 | 6/2019 | Cogswell et al. |
| 10,316,091 B2 | 6/2019 | Cogswell et al. |
| 10,323,093 B2 | 6/2019 | Cogswell et al. |
| 2006/0110383 A1 | 5/2006 | Honjo et al. |
| 2009/0217401 A1 | 8/2009 | Korman et al. |
| 2009/0297518 A1 | 12/2009 | Honjo et al. |
| 2011/0081341 A1 | 4/2011 | Honjo et al. |
| 2012/0263677 A1 | 10/2012 | Eagle et al. |
| 2013/0017199 A1 | 1/2013 | Langermann et al. |
| 2013/0133091 A1 | 5/2013 | Korman et al. |
| 2013/0309250 A1 | 11/2013 | Cogswell et al. |
| 2014/0212422 A1 | 7/2014 | Korman et al. |
| 2014/0294852 A1 | 10/2014 | Korman et al. |
| 2014/0314714 A1 | 10/2014 | Honjo et al. |
| 2014/0328833 A1 | 11/2014 | Korman et al. |
| 2014/0341917 A1 | 11/2014 | Nastri et al. |
| 2014/0348743 A1 | 11/2014 | Korman et al. |
| 2014/0356353 A1 | 12/2014 | Queva et al. |
| 2015/0079109 A1 | 3/2015 | Li et al. |
| 2015/0093380 A1 | 4/2015 | Honjo et al. |
| 2015/0125463 A1 | 5/2015 | Cogswell et al. |
| 2015/0165025 A1 | 6/2015 | Korman et al. |
| 2015/0197572 A1 | 7/2015 | Honjo et al. |
| 2016/0090417 A1 | 3/2016 | Cogswell et al. |
| 2016/0158355 A1 | 6/2016 | Honjo et al. |
| 2016/0158356 A1 | 6/2016 | Honjo et al. |
| 2016/0376367 A1 | 12/2016 | Yuan et al. |
| 2017/0051060 A1 | 2/2017 | Honjo et al. |
| 2017/0088615 A1 | 3/2017 | Korman et al. |
| 2018/0273624 A1 | 9/2018 | Cogswell et al. |
| 2018/0282413 A1 | 10/2018 | Cogswell et al. |
| 2018/0282414 A1 | 10/2018 | Cogswell et al. |
| 2018/0312590 A1 | 11/2018 | Cogswell et al. |
| 2018/0319887 A1 | 11/2018 | Cogswell et al. |
| 2019/0092863 A1 | 3/2019 | Cogswell et al. |
| 2019/0100589 A1 | 4/2019 | Cogswell et al. |
| 2019/0100590 A1 | 4/2019 | Cogswell et al. |
| 2019/0112376 A1 | 4/2019 | Cogswell et al. |
| 2019/0112377 A1 | 4/2019 | Cogswell et al. |
| 2019/0135920 A1 | 5/2019 | Cogswell et al. |
| 2019/0153099 A1 | 5/2019 | Cogswell et al. |

FOREIGN PATENT DOCUMENTS

| | | |
|---|---|---|
| WO | WO-200711364 A2 | 10/2007 |
| WO | WO-2012122444 A1 | 9/2012 |
| WO | WO-2012145493 A1 | 10/2012 |
| WO | WO-2013173223 A1 | 11/2013 |
| WO | WO-2014179664 A2 | 11/2014 |
| WO | WO-2014194302 A2 | 12/2014 |
| WO | WO-2015085847 A1 | 6/2015 |
| WO | WO-2015112800 A1 | 7/2015 |
| WO | WO-2015112900 A1 | 7/2015 |
| WO | WO-2016149201 A2 | 9/2016 |

OTHER PUBLICATIONS

Ansell, S.M., et al., "PD-1 Blockade With Nivolumab in Relapsed or Refractory Hodgkin's Lymphoma," The New England Journal of Medicine 372(4):311-319, Massachusetts Medical Society, United States (Jan. 2015).

Armand, P., et al., "Disabling Immune Tolerance by Programmed Death-1 Blockade With Pidilizumab After Autologous Hematopoietic Stem-cell Transplantation for Diffuse Large B-cell Lymphoma: Results of an International Phase II Trial," Journal of Clinical Oncology 31(33):4199-4206, American Society of Clinical Oncology, United States (Nov. 2013).

Brahmer, J.R., et al., "Safety and Activity of Anti-PD-L1 Antibody in Patients with Advanced Cancer," The New England Journal of Medicine 366(26):2455-2465, Massachusetts Medical Society, United States (Jun. 2012).

Brahmer., J.R., et al., "Phase I Study of Single-agent Anti-programmed Death-1 (MDX-1106) in Refractory Solid Tumors: Safety, Clinical Activity, Pharmacodynamics, and Immunologic Correlates," Journal of Clinical Oncology 28(19):3167-3175, American Society of Clinical Oncology, United States (Jul. 2010).

Chen, B.J., et al., "PD-L1 Expression Is Characteristic of a Subset of Aggressive B-cell Lymphomas and Virus-associated Malignancies," Clinical Cancer Research 19(13):3462-3473, The Association, United States (Jul. 2013).

Condeelis, J. and Weissleder, R., "In Vivo Imaging in Cancer," Cold Spring Harbor Perspectives in Biology 2(12):a003848, Cold Spring Harbor Laboratory Press, United States (Dec. 2010).

Drake, "Safety, Durable Clinical Benefit, and Remission Resulting from Nivolumanb (Anti-PD-1; BMS-936558; ONO-4538) in a Phase 1 Trial in Patients With Previously Treated Metastatic Renal Cell Carcinoma (mRCC); Long-Term Patient Follow-Up, Abstracts of the 12th International Kidney Cancer Symposium. Oct. 25-26, 2013. Chicago, Illinois, USA," BJU International 112 (Suppl 3):1-17, Blackwell Science, England (Nov. 2013).

GenBank, "cytotoxic T-lymphocyte-associated protein 4 [*Homo sapiens*]," Accession No. AAB59385.1, accessed on https://www.ncbi.nlm.nih.gov/protein/AAB59385, Nov. 1, 1994.

GenBank, "Human hPD-1 (hPD-1) mRNA, complete cds," Accession No. U64863.1, accessed on https://www.ncbi.nlm.nih.gov/nuccore/U64863, Oct. 12, 2005.

GenBank, "RecName: Full=Programmed cell death 1 ligand 1; Short=PD-L1; Short=PDCD1 ligand 1; Short=Programmed death ligand 1; AltName: Full=B7 homolog 1; Short=B7-H1; AltName: CD_antigen=CD274; Flags: Precursor," Accession No. Q9NZQ7.1, accessed on https://www.ncbi.nlm.nih.gov/protein/Q9NZQ7, Nov. 2, 2016.

Green, M.R., et al., "Constitutive AP-1 Activity and EBV Infection Induce PD-L1 in Hodgkin Lymphomas and Posttransplant Lymphoproliferative Disorders: Implications for Targeted Therapy," Clinical Cancer Research 18(6):1611-1618, The Association, United States (Mar. 2012).

Green, M.R., et al., "Integrative Analysis Reveals Selective 9p24.1 Amplification, Increased PD-1 Ligand Expression, and Further Induction via JAK2 in Nodular Sclerosing Hodgkin Lymphoma and Primary Mediastinal Large B-cell Lymphoma," Blood 116(17):3268-3277, American Society of Hematology, United States (Oct. 2010).

Herbst, R.S., et al., "A Study of MPDL3280A, an Engineered PD-L1 Antibody in Patients with Locally Advanced or Metastatic Tumors," Journal of Clinical Oncology 31(Suppl):Abstract 3000, American Society of Clinical Oncology, United States (2013).

Hodi, F.S., et al., "Improved Survival with Ipilimumab in Patients with Metastatic Melanoma," The New England Journal of Medicine 363(8):711-723, Massachusetts Medical Society, United States (Aug. 2010).

International Search report and Written opinion for Application No. PCT/US2017/035492, dated Aug. 4, 2017, 8 pages.

Johnson, D.B., et al., "Severe Cutaneous and Neurologic Toxicity in Melanoma Patients during Vemurafenib Administration Following Anti-PD-1 Therapy," Cancer Immunology Research 1(6):373-377, American Association for Cancer Research, United States (Dec. 2013).

Juszczynski, P., et al., "The AP1-dependent Secretion of Galectin-1 by Reed Sternberg Cells Fosters Immune Privilege in Classical Hodgkin Lymphoma," Proceedings of the National Academy of Sciences of the United States of America 104(32):13134-13139, National Academy of Sciences, United States (Aug. 2007).

Khleif, S., et al., "MEDI4736, An Anti-PD-L1 Antibody with Modified Fc Domain: Preclinical Evaluation and Early Clinical Results from a Phase 1 Study in Patients with Advanced Solid Tumors," Abstract 802, in Proceedings from the European Cancer Congress 2013, Amsterdam, The Netherlands (Sep. 27-Oct. 1, 2013).

Kuppers, R., "The Biology of Hodgkin's Lymphoma," Nature Reviews. Cancer 9(1):15-27, Nature Pub. Group, England (Jan. 2009).

Kuruvilla, J., et al., "How I Treat Relapsed and Refractory Hodgkin Lymphoma," Blood 117(16):4208-4217, American Society of Hematology, United States (Apr. 2011).

(56) References Cited

OTHER PUBLICATIONS

McCabe, K.E. and Wu, A.M., "Positive Progress in ImmunoPET--not Just a Coincidence," Cancer Biotherapy & Radiopharmaceuticals 25(3):253-261, Mary Ann Liebert, Inc, United States (Jun. 2010).
National Cancer Institute, Drugs Approved for Hodgkin Lymphoma, accessed at http://www.cancer.gov/about-cancer/treatment/drugs/hodgkin-lymphoma, accessed on May 27, 2016.
NCI Drug Dictionary, anti-PD-1 Fusion Protein AMP-224, accessed on Dec. 01, 2016, retrieved from the Internet URL: https://www.cancer.gov/publications/dictionaries/cancer-drug?cdrid=700595.
NCI Drug Dictionary, anti-PD-1 monoclonal antibody MEDI0680, accessed on Dec. 1, 2016, retrieved from the Internet URL: https://www.cancer.gov/publications/dictionaries/cancer-drug?cdrid=756047.
NCI Drug Dictionary, pembrolizumab, accessed on Dec. 1, 2016, retrieved from the Internet URL: https://www.cancer.gov/drugdictionary?cancer-drug?cdrid=695789, 3 pages.
Olafsen, T., et al., "ImmunoPET Imaging of B-Cell Lymphoma Using 124I-Anti-CD20 scFv Dimers (Diabodies)," Protein Engineering, Design & Selection 23(4):243-249, Oxford University Press, England (Apr. 2010).
Rini, B.I., et al., "Phase 1 Dose-escalation Trial of Tremelimumab Plus Sunitinib in Patients with Metastatic Renal Cell Carcinoma," Cancer 117(14):758-767, Wiley, United States (Feb. 2011).
Sjoblom, T., et al., "The Consensus Coding Sequences of Human Breast and Colorectal Cancers," Science 314(5797):268-274, American Association for the Advancement of Science, United States (Oct. 2006).
Steidl, C., et al., "MHC Class II Transactivator CIITA is a Recurrent Gene Fusion Partner in Lymphoid Cancers," Nature 471(7338):377-381, Nature Publishing Group, England (2011).
Taube, J.M., et al., "Association of PD-1, PD-1 Ligands, and Other Features of the Tumor Immune Microenvironment With Response to Anti-PD-1 Therapy," Clinical Cancer Research 20(19):5064-5074, The Association, United States (Oct. 2014).
Taube, J.M., et al., "Colocalization of Inflammatory Response with B7-H1 Expression in Human Melanocytic Lesions Supports an Adaptive Resistance Mechanism of Immune Escape," Science Translational Medicine 4(127):127ra37, American Association for the Advancement of Science, United States (Mar. 2012).
Topalian, S.L., et al., "Safety, Activity and Immune Correlates of Anti-PD-1 Antibody in Cancer," The New England Journal of Medicine 366(26):2443-2454, Massachusetts Medical Society, United States (Jun. 2012).
Topalian, S.L., et al., "Targeting the PD-1/67-H1(PD-L1) Pathway to Activate Anti-tumor Immunity," Current Opinion in Immunology 24(2):207-212, Elsevier, England (Apr. 2012).
Topalian, S.L., et al., "Survival, Durable Tumor Remission, and Long-term Safety in Patients with Advanced Melanoma Receiving Nivolumab," Journal of Clinical Oncology 32(10):1020-1030, American Society of Clinical Oncology, United States (Apr. 2014).
Wang, C., et al., "In Vitro Characterization of the Anti-PD-1 Antibody Nivolumab, BMS-936558, and in Vivo Toxicology in Non-human Primates," Cancer Immunology Research 2(9):846-856, American Association for Cancer Research, United States (Sep. 2014).
Wolchok, J.D., et al., "Nivolumab Plus Ipilimumab in Advanced Melanoma," The New England Journal of Medicine 369(2):122-133, Massachusetts Medical Society, United States (Jul. 2013).
Ramchandren et al., "Nivolumab for newly diagnosed advanced-stage classic Hodgkin lymphoma: safety and efficacy in the phase II CheckMate 205 study," *JCO* 37(23):1997-2007 (Aug. 10, 2019).
Younes, Anas, et al. "Checkmate 205: Nivolumab (nivo) in classical Hodgkin lymphoma (cHL) after autologous stem cell transplant (ASCT) and brentuximab vedotin (BV)—A phase 2 study." 7535-7535, American Society of Clinical Oncology (May 20, 2016).
Moskowitz, Craig H., et al. "PD-1 blockade with the monoclonal antibody pembrolizumab (MK-3475) in patients with classical Hodgkin lymphoma after brentuximab vedotin failure: preliminary results from a phase 1b study (KEYNOTE-013)." Blood 124(21): 290-290, American Society of Hematology (2014).
Younes, Anas, et al. "Brentuximab vedotin combined with ABVD or AVD for patients with newly diagnosed Hodgkin's lymphoma: a phase 1, open-label, dose-escalation study." The Lancet Oncology 14(13): 1348-1356, Elsevier, Netherlands (2013).
Yoshida, Takao, et al. "Pharmacological Profile and Clinical Efficacy of Human Anti-Human PD-1 Antibody Nivolumab (OPDIVO®) as a New Immune Checkpoint Inhibitor." Nihon yakurigaku zasshi. Folia Pharmacologica Japonica 146(2): 106-114, Japanese Pharmacological Society (2015).
Maly, Joseph, and Lapo Alinari. "Pembrolizumab in classical Hodgkin's lymphoma." European Journal of Haematology 97(3): 219-227, Wiley-Blackwell Publishing, England (2016).

\* cited by examiner

TREATMENT OF HODGKIN LYMPHOMA USING AN ANTI-PD-1 ANTIBODY

FIELD OF THE DISCLOSURE

This disclosure relates to methods for treating Hodgkin lymphoma in a subject in need thereof comprising administering to the subject an anti-Programmed Death-1 (PD-1) antibody or an antigen binding portion thereof, wherein the subject has received at least one prior treatment for Hodgkin lymphoma selected from the group consisting of an autologous stem cell therapy, brentuximab vedotin, and both.

BACKGROUND OF THE DISCLOSURE

Human cancers harbor numerous genetic and epigenetic alterations, generating neoantigens potentially recognizable by the immune system (Sjoblom et al., (2006) *Science* 366:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

Until recently, cancer immunotherapy had focused substantial effort on approaches that enhance anti-tumor immune responses by adoptive-transfer of activated effector cells, immunization against relevant antigens, or providing non-specific immune-stimulatory agents such as cytokines. In the past decade, however, intensive efforts to develop specific immune checkpoint pathway inhibitors have begun to provide new immunotherapeutic approaches for treating cancer Nivolumab (formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., (2014) *Cancer Immunol Res* 2:846-56). Nivolumab has shown activity in a variety of advanced solid tumors including renal cell carcinoma (renal adenocarcinoma, or hypernephroma), melanoma, and non-small cell lung cancer (NSCLC) (Topalian et al., (2012) *N Engl J Med* 366:2443-54; Topalian et al., (2014) *J Clin Oncol* 32:1020-30; Drake et al., (2013) *BJU Int* 112:1-17; Ansell et al., (2015) *Blood* 126:583 [Abstract]; PCT Publication No. WO 2013/173223).

In order to survive in an immunocompetent host, many human cancers have evolved mechanisms to disable immune responses against tumor neoantigens. For instance, classical Hodgkin lymphoma (cHL), a B-cell malignancy that commonly affects young adults, is characterized by small numbers of neoplastic Reed-Sternberg (RS) cells within an extensive inflammatory/immune cell infiltrate. (Green et al., (2010) *Blood* 116:3268-77). However, there is little evidence of an effective antitumor immune response, suggesting that immune evasion pathways may play a role in the tumor's survival in the host. Indeed, the Hodgkin RS (HRS) cells express molecules that limit the efficacy of T cell responses. (Juszczynski et al., (2007) *Proc Natl Acad Sci USA* 104:13134-9; and Kuppers, (2009) *Nat Rev Cancer* 9:15-27).

Classic Hodgkin's lymphomas include small numbers of malignant Reed-Sternberg cells within an extensive but ineffective inflammatory and immune-cell infiltrate. (Taube et al., (2014) *Clin Cancer Res* 20:5064-74; Topalian et al., (2014) *J Clin Oncol* 32:1020-30). The genes encoding the PD-1 ligands, PD-L1 and PD-L2 (also called CD274 and PDCD1LG2, respectively), are key targets of chromosome 9p24.1 amplification, a recurrent genetic abnormality in Hodgkin lymphoma. (Taube et al., (2014) *Clin Cancer Res* 20:5064-74). The 9p24.1 amplicon also includes JAK2, and gene dosage-dependent JAK-STAT activity further induces PD-1 ligand transcription. (Green et al., (2010) *Blood* 116: 3268-77). The genes encoding the PD-1 ligands, PDL1 and PDL2 (also called CD274 and PDCD1LG2, respectively), are key targets of chromosome 9p24.1 amplification, a recurrent genetic abnormality in the nodular-sclerosis type of Hodgkin lymphoma. (Taube et al., (2014) *Clin Cancer Res* 20:5064-74), and recent analysis integrating high-resolution copy-number data and transcriptional profiles identified PD-L1 and PD-L2 as key targets of chromosome 9p24.1 amplification. (Green et al., (2010) *Blood* 116:3268-77). These copy-number-dependent mechanisms, as well as other less frequent rearrangements, lead to genetically determined overexpression of the PD-1 ligands on the HRS cell surface. (Steidl et al., (2011) *Nature* 471:377-81; Andorsky et al., (2011) *Clin Cancer Res* 17:4232-44).

Epstein-Barr virus (EBV) infection, also common in cHL, is an additional mechanism of PD-L1 overexpression, consistent with the virus's known ability to usurp the PD-1 pathway to allow viral persistence in the host. (Green et al., (2012) *Clin Cancer Res* 18:1611-8). Therefore, Epstein-Barr virus (EBV) infection also increases the expression of PD-1 ligands in EBV-positive Hodgkin lymphomas. (Armand et al., (2013) *J Clin Oncology* 31:4199-206). As a result of the two complementary pathways of 9p24.1 alterations and EBV infection, over 80% of cHL cases have increased surface expression of PD-L1, suggesting a central role for the PD-1 pathway in this disease. (Chen et al., (2013) *Clin Cancer Res* 19:3462-73).

Current treatments for cHL primarily include chemotherapy, radiation therapy, and stem cell/bone marrow transplantation. Despite such treatment options, many cHL patients fail to achieve complete remission or subsequently relapse after treatment. (Kuruvilla et al., (2011) *Blood* 117:4208-17). Therefore, a more effective treatment option is required for cHL and other human cancers.

SUMMARY OF THE DISCLOSURE

The present disclosure relates to a method for treating a subject afflicted with a tumor derived from a Hodgkin lymphoma comprising administering to the subject a therapeutically effective amount of an antibody or an antigen-binding portion thereof that binds specifically to a Programmed Death-1 receptor (PD-1) ("anti-PD-1 antibody"), wherein the subject was not responsive to a prior treatment selected from (i) an autologous stem cell therapy, (ii) brentuximab vedotin, and both (i) and (ii).

In some embodiments, the subject failed to achieve a partial response after the prior treatment. In certain embodiments, the subject had a relapse after a complete response after the prior treatment. In one embodiment, the subject had progressive disease after a partial response or stable disease after the prior treatment. In an embodiment, the subject is further administered doxorubicin, vinblastine, and dacarbazine.

The present disclosure relates to a method for treating a subject afflicted with a tumor derived from a Hodgkin lymphoma comprising administering to the subject a therapeutically effective amount of an anti-PD-1 antibody in combination with doxorubicin, vinblastine, and dacarbazine.

In further embodiments, the subject is not administered bleomycin. In certain embodiments, the doxorubicin, vinblastine, and dacarbazine are administered once about every one, two, three, or four weeks. In some embodiments, the doxorubicin is administered at a dose of about 10 mg/m$^2$ to about 40 mg/m$^2$, about 10 mg/m$^2$ to about 30 mg/m$^2$, or about 20 mg/m$^2$ to about 30 mg/m$^2$, the vinblastine is administered at a dose of about 0.1 mg/m$^2$ to about 10 mg/m$^2$, about 1 mg/m$^2$ to about 10 mg/m$^2$, or about 5 mg/m$^2$ to about 10 mg/m$^2$, and/or the dacarbazine is administered at a dose of about 200 mg/m$^2$ to about 500 mg/m$^2$, about 250 mg/m$^2$ to about 500 mg/m$^2$, or about 300 mg/m$^2$ to about 400 mg/m$^2$. In particular embodiments, the doxorubicin is administered at a dose of 25 mg/m$^2$, the vinblastine is administered at a dose of 6 mg/m$^2$, and the dacarbazine is administered at a dose of 375 mg/m$^2$ once about every 2 weeks.

In some embodiments, the anti-PD-1 antibody cross-competes with nivolumab for binding to human PD-1. In other embodiments, the anti-PD-1 antibody binds to the same epitope as nivolumab. In further embodiments, the anti-PD-1 antibody is a chimeric, humanized, or human monoclonal antibody or a portion (e.g., an antigen-binding portion) thereof. In still further embodiments, the anti-PD-1 antibody comprises a heavy chain constant region which is of a human IgG1 or IgG4 isotype. In some embodiments, the anti-PD-1 antibody is nivolumab. In other embodiments, the anti-PD-1 antibody is pembrolizumab.

In particular embodiments, the anti-PD-1 antibody is administered at a dose ranging from at least about 0.1 mg/kg to at least about 10.0 mg/kg body weight once about every 1, 2, or 3 weeks. In further embodiments, the anti-PD-1 antibody (e.g., nivolumab) is administered at a dose of at least about 3 mg/kg body weight once about every 2 weeks. In other embodiments, the anti-PD-1 antibody (e.g., pembrolizumab) is administered at a dose of at least about 200 mg every 3 weeks or 2 mg/kg (up to 200 mg) every three weeks. In some embodiments, the anti-PD-1 antibody (e.g., avelumab) is administered at a dose of 10 mg/kg every two weeks. In certain embodiments, the anti-PD-1 antibody is administered at a flat dose. In embodiments, the anti-PD-1 antibody is administered at a flat dose of at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, at least about 550 mg, at least about 600 mg, at least about 650 mg, at least 700 mg, at least 750 mg, or at least 800 mg. In some embodiments, the anti-PD-1 antibody is administered at a flat dose about once every 1, 2, 3, or 4 weeks. In particular embodiments, the anti-PD-1 antibody is administered at a subtherapeutic dose. In some embodiments, the anti-PD-1 antibody is administered for as long as clinical benefit is observed or until unmanageable toxicity or disease progression occurs. In certain embodiments, the anti-PD-1 antibody is formulated for intravenous administration.

In some embodiments, the method further comprises administering one or more additional anti-cancer agents.

In some embodiments, the Hodgkin lymphoma has a genetic alteration at 9p24.1. In particular embodiments, the Hodgkin lymphoma expresses PD-L1 and/or PD-L2.

In some embodiments, the PD-L1 and/or PD-L2 expression is at least about 1%. In other embodiments, the PD-L1 and/or PD-L2 expression of the tumor is at least about 5%. In further embodiments, the PD-L1 and/or PD-L2 expression of the tumor is at least about 10%. In embodiments, the PD-L1 and/or PD-L2 expression is measured by automated immunohistochemistry (IHC) or fluorescent in situ hybridization.

In particular embodiments, the subject exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the initial administration. In other embodiments, the subject exhibits an overall survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the initial administration.

The disclosure relates to a kit for treating a subject afflicted with a tumor derived from a Hodgkin lymphoma who has received at least one prior treatment for Hodgkin lymphoma, the kit comprising: (a) an anti-PD-1 antibody; and (b) instructions for administering the anti-PD-1 antibody to the subject in any method disclosed herein.

In certain embodiments, the kit optionally comprises an additional step between (a) and (b): instructions for determining the PD-L1 and/or PD-L2 expression of the tumor. In some embodiments, the kit comprises an agent to determine the PD-L1 and/or PD-L2 expression of the tumor. In some embodiments, the PD-L1 and/or PD-L2 expression is measured by an anti-PD-L1 and/or PD-L2 antibody.

Other features and advantages of the instant disclosure will be apparent from the following detailed description and examples which should not be construed as limiting. The contents of all cited references, including scientific articles, newspaper reports, GenBank entries, patents and patent applications cited throughout this application are expressly incorporated herein by reference.

EMBODIMENTS

E1. A method for treating a subject afflicted with a tumor derived from a Hodgkin's lymphoma comprising administering to the subject a therapeutically effective amount of an antibody or an antigen-binding portion thereof that binds specifically to a Programmed Death-1 receptor (PD-1) ("anti-PD-1 antibody"), wherein the subject was not responsive to a prior treatment selected from (i) an autologous stem cell therapy, (ii) brentuximab vedotin, and both (i) and (ii).

E2. The method of embodiment E1, wherein the subject failed to achieve a partial response after the prior treatment.

E3. The method of embodiment E1 or E2, wherein the subject had a relapse after a complete response after the prior treatment.

E4. The method of any one of embodiments E1 to E3, wherein the subject had progressive disease after a partial response or stable disease after the prior treatment.

E5. The method of any one of embodiments E1 to E4, wherein the subject is further administered doxorubicin, vinblastine, and dacarbazine.

E6. A method for treating a subject afflicted with a tumor derived from a Hodgkin's lymphoma comprising administering to the subject a therapeutically effective amount of an anti-PD-1 antibody in combination with doxorubicin, vinblastine, and dacarbazine.

E7. The method of any one of embodiments E1-E6, wherein the subject is not administered bleomycin.

E8. The method of any one of embodiments E5 to E7, wherein the doxorubicin, vinblastine, and dacarbazine are administered once about every one, two, three or four weeks.

E9. The method of any one of embodiments E5 to E8, wherein the doxorubicin is administered at a dose of about 10 mg/m$^2$ to about 40 mg/m$^2$, about 10 mg/m$^2$ to about 30 mg/m$^2$, or about 20 mg/m$^2$ to about 30 mg/m$^2$, the vinblastine is administered at a dose of about 0.1 mg/m$^2$ to about 10 mg/m$^2$, about 1 mg/m$^2$ to about 10 mg/m$^2$, or about 5 mg/m$^2$ to about 10 mg/m$^2$, and/or the dacarbazine is administered at a dose of about 200 mg/m$^2$ to about 500 mg/m$^2$ about 250 mg/m$^2$ to about 500 mg/m$^2$, or about 300 mg/m$^2$ to about 400 mg/m$^2$.

E10. The method of any one of embodiments E5 to E9, wherein the doxorubicin is administered at a dose of 25 mg/m$^2$, the vinblastine is administered at a dose of 6 mg/m$^2$, and the dacarbazine is administered at a dose of 375 mg/m$^2$ once about every 2 weeks.

E11. The method of any one of embodiments E1 to E10, wherein the anti-PD-1 antibody cross-competes with nivolumab for binding to human PD-1.

E12. The method of any one of embodiments E1 to E11, wherein the anti-PD-1 antibody binds to the same epitope as nivolumab.

E13. The method of any one of embodiments E1 to E12, wherein the anti-PD-1 antibody is a chimeric, humanized or human monoclonal antibody or a portion thereof.

E14. The method of any one of embodiments E1 to E13, wherein the anti-PD-1 antibody comprises a heavy chain constant region which is of a human IgG1 or IgG4 isotype.

E15. The method of any one of embodiments E1 to E14, wherein the anti-PD-1 antibody is nivolumab.

E16. The method of any one of embodiments E1 to E14, wherein the anti-PD-1 antibody is pembrolizumab.

E17. The method of any one of embodiments E1 to E16, wherein the anti-PD-1 antibody is administered at a dose ranging from at least about 0.1 mg/kg to at least about 10.0 mg/kg body weight once about every 1, 2 or 3 weeks.

E18. The method of any one of embodiments E1 to E17, wherein the anti-PD-1 antibody is administered at a dose of at least about 3 mg/kg body weight once about every 2 weeks.

E19. The method of any one of embodiments E1 to E16, wherein the anti-PD-1 antibody is administered at a flat dose.

E20. The method of embodiment E19, wherein the anti-PD-1 antibody is administered at a flat dose of at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, or at least about 550 mg.

E21. The method of embodiment E19 or E20, wherein the anti-PD-1 antibody is administered at a flat dose about once every 1, 2, 3 or 4 weeks.

E22. The method of any one of embodiments E1 to E16, wherein the anti-PD-1 antibody is administered at a subtherapeutic dose.

E23. The method of any one of embodiments E1 to E22, wherein the anti-PD-1 antibody is administered for as long as clinical benefit is observed or until unmanageable toxicity or disease progression occurs.

E24. The method of any one of embodiments E1 to E23, wherein the anti-PD-1 antibody is formulated for intravenous administration.

E25. The method of any one of embodiments E1 to E24, which further comprises administering one or more additional anti-cancer agents.

E26. The method of any one of embodiments E1 to E25, wherein the Hodgkin's lymphoma has a genetic alteration at 9p24.1.

E27. The method of any one of embodiments E1 to E26, wherein the Hodgkin's lymphoma expresses PD-L1 and/or PD-L2.

E28. The method of any one of embodiments E1 to E27, wherein the PD-L1 and/or PD-L2 expression is at least about 1%.

E29. The method of any one of embodiments E1 to E28, wherein the PD-L1 and/or PD-L2 expression of the tumor is at least about 5%.

E30. The method of any one of embodiments E1 to E29, wherein the PD-L1 and/or PD-L2 expression of the tumor is at least about 10%.

E31. The method of any one of embodiments E1 to E30, wherein the PD-L1 and/or PD-L2 expression is measured by automated immunohistochemistry (IHC) or fluorescent in situ hybridization.

E32. The method of any one of embodiments E1 to E31, wherein the subject exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the initial administration.

E33. The method of any one of embodiments E1 to E32, wherein the subject exhibits an overall survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the initial administration.

E34. A kit for treating a subject afflicted with a tumor derived from a Hodgkin's lymphoma who has received at least one prior treatment for Hodgkin's lymphoma, the kit comprising: (a) an anti-PD-1 antibody; and (b) instructions for administering the anti-PD-1 antibody to the subject in the methods of embodiments E1 to E33.

E35. The kit of embodiment E34, optionally comprising an additional step between (a) and (b): instructions for determining the PD-L1 and/or PD-L2 expression of the tumor.

E36. The kit of embodiment E35, further comprising an agent to determine the PD-L1 and/or PD-L2 expression of the tumor.

E37. The kit of embodiment E35 or E36, wherein the PD-L1 and/or PD-L2 expression is measured by an anti-PD-L1 and/or PD-L2 antibody.

BRIEF DESCRIPTION OF THE DRAWINGS

FIG. 2A shows the response characteristics in all responders (n=53) per IRRC assessment. Of the responders, 62% continued to respond at time of analysis (denoted by a black arrow). The median time to response was 2.1 months (1.6-5.7 months) and the median duration of response was 7.8 months (6.6 months—not estimable). FIG. 2B shows the independent radiologic review committee (IRRC) assessment of the best change from baseline in tumor burden for all response-evaluable patients. All but one responder had a reduction of greater than 50% from baseline in tumor burden, and the patient who didn't had a negative CDG-PET scan. FIG. 2C shows the change in tumor burden in patients treated with nivolumab beyond progression. Of the 9 patients analyzed, 6 patients maintained tumor reduction, per investigator assessment.

DETAILED DESCRIPTION OF THE DISCLOSURE

Figure 1:
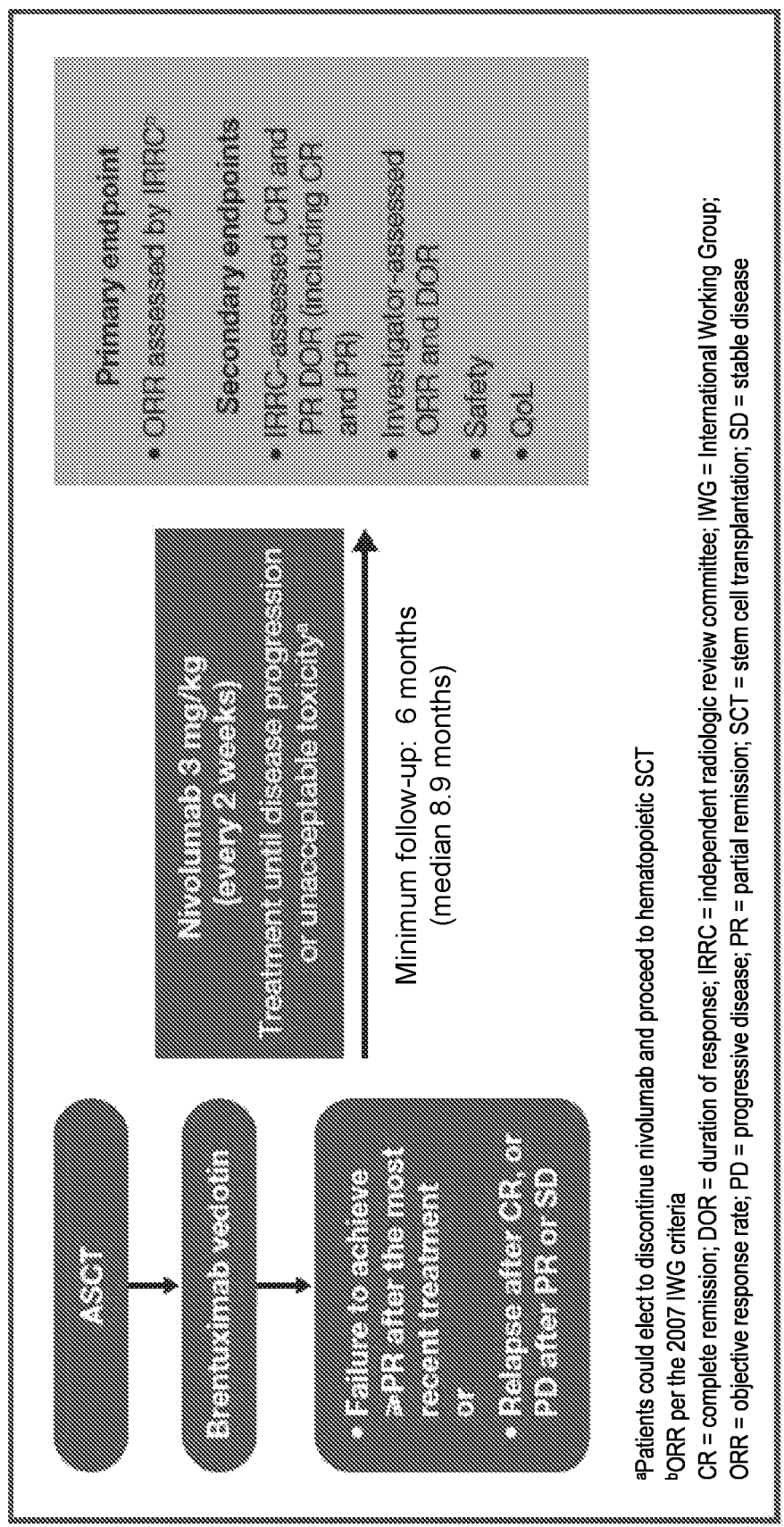
FIG. 1 shows a study design schematic for a Multicenter, Non-Comparative Phase 2 Registrational Study assessing the efficacy and safety of nivolumab monotherapy in classical Hodgkin lymphoma (cHL) patients after failed treatment with autologous stem cell transplantation and brentuximab vedotin.

The present disclosure relates to the superior effects of an anti-PD-1 antibody or anti-PD-L1 antibody in treating a patient with Classical Hodgkin Lymphoma (cHL) who has received at least one prior treatment. The present methods for treating a Classical Hodgkin Lymphoma (cHL) patient comprise administering to the patient an anti-PD-1 antibody or an anti-PD-L1 antibody.

Terms

In order that the present disclosure can be more readily understood, certain terms are first defined. As used in this application, except as otherwise expressly provided herein, each of the following terms shall have the meaning set forth below. Additional definitions are set forth throughout the application.

"Administering" refers to the physical introduction of a composition comprising a therapeutic agent to a subject, using any of the various methods and delivery systems known to those skilled in the art. Routes of administration for the anti-PD-1 antibody include intravenous, intramuscular, subcutaneous, intraperitoneal, spinal, or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural, and intrasternal injection and infusion, as well as in vivo electroporation. In some embodiments, a composition is administered via a non-parenteral route, in some embodiments, orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. For example, an adverse event can be associated with activation of the immune system or expansion of immune system cells (e.g., T cells) in response to a treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises at least three constant domains, $C_{H1}$, $C_{H2}$ and $C_{H3}$. Each light chain comprises a light chain variable region (abbreviated herein as $V_L$) and a light chain constant region. The light chain constant region is comprises one constant domain, $C_L$. The $V_H$ and $V_L$ regions can be further subdivided into regions of hypervariability, termed complementarity determining regions (CDRs), interspersed with regions that are more conserved, termed framework regions (FRs). Each $V_H$ and $V_L$ comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

An immunoglobulin can derive from any of the commonly known isotypes, including but not limited to IgA, secretory IgA, IgG, and IgM. IgG subclasses are also well known to those in the art and include but are not limited to human IgG1, IgG2, IgG3, and IgG4. "Isotype" refers to the antibody class or subclass (e.g., IgM or IgG1) that is encoded by the heavy chain constant region genes. The term "antibody" includes, by way of example, both naturally occurring and non-naturally occurring antibodies; monoclonal and polyclonal antibodies; chimeric and humanized antibodies; human or non-human antibodies; wholly synthetic antibodies; and single chain antibodies. A non-human antibody can be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

An "isolated antibody" refers to an antibody that is substantially free of other antibodies having different antigenic specificities (e.g., an isolated antibody that binds specifically to PD-1 is substantially free of antibodies that bind specifically to antigens other than PD-1). An isolated antibody that binds specifically to PD-1 can, however, have cross-reactivity to other antigens, such as PD-1 molecules from different species. Moreover, an isolated antibody can be substantially free of other cellular material and/or chemicals.

The term "monoclonal antibody" (mAb) refers to a non-naturally occurring preparation of antibody molecules of single molecular composition, i.e., antibody molecules whose primary sequences are essentially identical, and which exhibits a single binding specificity and affinity for a particular epitope. A monoclonal antibody is an example of an isolated antibody and can be produced by hybridoma, recombinant, transgenic, or other techniques known to those skilled in the art.

A "human antibody" (HuMAb) refers to an antibody having variable regions in which both the framework and CDRs are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human antibodies" and "fully human antibodies" are used synonymously.

A "humanized antibody" refers to an antibody in which some, most, or all of the amino acids outside the CDRs of a non-human antibody are replaced with corresponding amino acids derived from human immunoglobulins. In one embodiment of a humanized form of an antibody, some, most or all of the amino acids outside the CDRs have been replaced with amino acids from human immunoglobulins, whereas some, most or all amino acids within one or more CDRs are unchanged. Small additions, deletions, insertions, substitutions or modifications of amino acids are permissible as long as they do not abrogate the ability of the antibody to bind to a particular antigen. A "humanized antibody" retains an antigenic specificity similar to that of the original antibody. In some embodiments, the CDRs of a humanized antibody contain CDRs from a non-human, mammalian antibody. In other embodiments, the CDRs of a humanized antibody contain CDRs from an engineered, synthetic antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen" antibody refers to an antibody that binds specifically to the antigen. For example, an anti-PD-1 antibody binds specifically to PD-1 and an anti-CTLA-4 antibody binds specifically to CTLA-4.

An "antigen-binding portion" of an antibody (also called an "antigen-binding fragment") refers to one or more fragments of an antibody that retain the ability to bind specifically to the antigen bound by the whole antibody.

A "cancer" refers a broad group of various diseases characterized by the uncontrolled growth of abnormal cells in the body. A "cancer" or "cancer tissue" can include a tumor. Unregulated cell division and growth results in the formation of malignant tumors that invade neighboring tissues and may also metastasize to distant parts of the body through the lymphatic system or bloodstream. Following metastasis, the distal tumors can be said to be "derived from" the original, pre-metastasis tumor. For example, a "tumor derived from" a non-Hodgkin Lymphoma refers to a tumor that is the result of a metastasized non-Hodgkin Lymphoma. Because the distal tumor is derived from the pre-metastasis tumor, the "derived from" tumor can also comprise the pre-metastasis tumor, e.g., a tumor derived from a non-Hodgkin Lymphoma can comprise a non-Hodgkin Lymphoma. In some embodiments, the cancer is Hodgkin lymphoma (also referring to as Hodgkin lymphoma, Classical Hodgkin Lymphoma and CHL).

"Cytotoxic T-Lymphocyte Antigen-4" (CTLA-4) refers to an immunoinhibitory receptor belonging to the CD28 family. CTLA-4 is expressed exclusively on T cells in vivo, and binds to two ligands, CD80 and CD86 (also called B7-1 and B7-2, respectively). The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. AAB59385.

The term "immunotherapy" refers to the treatment of a subject afflicted with, or at risk of contracting or suffering a recurrence of, a disease by a method comprising inducing, enhancing, suppressing or otherwise modifying an immune response.

"Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

"PD-L1 positive" or "PD-L2 positive" as used herein can be interchangeably used with "PD-L1 and/or PD-L2 expression of at least about 1%." In one embodiment, the PD-L1 and/or PD-L2 expression can be used by any methods known in the art. In another embodiment, the PD-L1 and/or PD-L2 expression is measured by an automated in situ hybridization (IHC). A PD-L1 and/or PD-L2 positive tumor can thus have at least about 1%, at least about 2%, at least about 5%, at least about 10%, or at least about 20%, at least about 25%, at least about 30%, at least about 40%, at least about 50%, at least about 60%, at least about 70%, at least about 75%, at least about 80%, at least about 85%, at least about 90%, at least about 95%, or about 100% of tumor cells expressing PD-L1 and/or PD-L2 as measured by an automated IHC. In certain embodiments, "PD-L1 positive" means that there are at least 100 cells that express PD-L1 on the surface of the cells. In other embodiments, "PD-L2 positive" means that there are at least 100 cells that express PD-L2 on the surface of the cells.

"Programmed Death-1" (PD-1) refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1" (PD-L1) is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

A "subject" includes any human or non-human animal. The term "non-human animal" includes, but is not limited to, vertebrates such as non-human primates, sheep, dogs, and rodents such as mice, rats and guinea pigs. In some embodiments, the subject is a human. The terms, "subject" and "patient" are used interchangeably herein.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

As used herein, "subtherapeutic dose" means a dose of a therapeutic compound (e.g., an antibody) that is lower than the usual or typical dose of the therapeutic compound when administered alone for the treatment of a hyperproliferative disease (e.g., cancer).

By way of example, an "anti-cancer agent" promotes cancer regression in a subject or prevents further tumor growth. In certain embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of an anti-cancer agent can inhibit cell growth or tumor growth by at least about 10%, at least about 20%, by at least about 30%, by at least about 40%, by at least about 50%, by at least about 60%, by at least about 70%, by at least about 80%, by at least about 90%, at least about 95%, or about 100% relative to untreated subjects or, in certain embodiments, relative to patients treated with a standard-of-care therapy. In other embodiments of the disclosure, tumor regression can be observed and continue for a period of at least about 20 days, at least about 30 days, at least about 40 days, at least about 50 days, or at least about 60 days. Notwithstanding these ultimate measurements of therapeutic effectiveness, evaluation of immunotherapeutic drugs must also make allowance for "immune-related response patterns".

An "immune-related response pattern" refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

A therapeutically effective amount of a drug includes a "prophylactically effective amount," which is any amount of the drug that, when administered alone or in combination with an anti-neoplastic agent to a subject at risk of developing a cancer (e.g., a subject having a pre-malignant condition) or of suffering a recurrence of cancer, inhibits the development or recurrence of the cancer. In certain embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

The term "weight-based dose" as referred to herein means that a dose that is administered to a patient is calculated based on the weight of the patient. For example, when a patient with 60 kg body weight requires 3 mg/kg of an anti-PD-1 antibody, one can calculate and use the appropriate amount of the anti-PD-1 antibody (i.e., 180 mg) for administration.

The use of the term "fixed dose" with regard to a method of the disclosure means that two or more different antibodies in a single composition (e.g., anti-PD-1 antibody and anti-CTLA-4 antibody) are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody (e.g., anti-PD-1 antibody) to mg second antibody (e.g., anti-CTLA-4 antibody). For example, the 3:1 ratio of an anti-PD-1 antibody and an anti-CTLA-4 antibody can mean that a vial can contain about 240 mg of the anti-PD-1 antibody and 80 mg of the anti-CTLA-4 antibody or about 3 mg/ml of the anti-PD-1 antibody and 1 mg/ml of the anti-CTLA-4 antibody.

The use of the term "flat dose" with regard to the methods and dosages of the disclosure means a dose that is administered to a patient without regard for the weight or body surface area (BSA) of the patient. The flat dose is therefore not provided as a mg/kg dose, but rather as an absolute amount of the agent (e.g., the anti-PD-1 antibody). For example, a 60 kg person and a 100 kg person would receive the same dose of an antibody (e.g., 240 mg of an anti-PD-1 antibody).

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The terms "once about every week," "once about every two weeks," or any other similar dosing interval terms as used herein mean approximate numbers. "Once about every week" can include every seven days±one day, i.e., every six days to every eight days. "Once about every two weeks" can include every fourteen days±three days, i.e., every eleven days to every seventeen days. Similar approximations apply, for example, to once about every three weeks, once about every four weeks, once about every five weeks, once about every six weeks and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

TABLE 1

List of Abbreviations

| Term | Definition |
| --- | --- |
| AEs | adverse events |
| ASCT | autologous stem cell transplantation |
| BMS | Bristol-Myers Squibb |

TABLE 1-continued

List of Abbreviations

| Term | Definition |
| --- | --- |
| cHL | classical Hodgkin lymphoma |
| CI | confidence interval |
| CR | complete remission |
| CT | computerized tomography (CT) scan |
| DOR | duration of response |
| EBV | Epstein-Barr virus |
| FDG | fluorodeoxyglucose |
| IRRC | independent radiologic review committee |
| Kg | kilogram |
| mAB | monoclonal antibody |
| Mg | milligram |
| MRI | magnetic resonance imaging |
| N | number of subjects or observations |
| NE | not evaluable |
| ORR | overall response rate |
| OS | overall survival |
| PD | progressive disease |
| PD-1 | programmed death-1 |
| PD-L1 | programmed death-ligand 1 |
| PD-L2 | programmed death-ligand 2 |
| PET | positron emission tomography |
| PFS | progression-free survival |
| PR | partial remission |
| QoL | quality of life |
| SAE | serious adverse event |
| SCT | stem cell transplantation |
| SD | stable disease |
| SOP | Standard Operating Procedures |
| Subj | subject |

Methods of the Disclosure

This disclosure provides a method of treating a subject afflicted with a tumor derived from Hodgkin lymphoma, wherein the subject has received (e.g., not responded to) at least one prior treatment for Hodgkin lymphoma selected from the group consisting of (i) an autologous stem cell therapy, (ii) brentuximab vedotin, and both (i) and (ii), wherein the method comprises administering to the subject a therapeutically effective amount of an antibody or an antigen-binding portion thereof that specifically binds to and a PD-1 receptor and inhibits PD-1 activity ("anti-PD-1 antibody") or an antibody or an antigen-binding portion thereof that specifically binds to and a PD-L1 receptor and inhibits PD-L1 activity ("anti-PD-L1 antibody").

In certain embodiments, the disclosure is directed to a method for treating a subject afflicted with a tumor derived from Hodgkin lymphoma wherein the subject has received at least one prior treatment for Hodgkin lymphoma selected from the group consisting of (i) an autologous stem cell therapy, (ii) an anti-CD30 antibody (e.g., brentuximab vedotin), and both (i) and (ii), comprising administering to the subject a therapeutically effective amount of: an anti-PD-1 antibody or an antigen-binding portion thereof or anti-PD-L1 antibody or an antigen binding portion thereof.

In some embodiments, the subject has received at least two prior treatments for Hodgkin lymphoma. In some embodiments, the prior treatment received by the patient was autologous stem cell transplantation. In other embodiments, the prior treatment received by the patient was an anti-CD30 antibody, e.g., brentuximab vedotin. In yet other embodiments, the patient received both autologous stem cell transplantation and an anti-CD30 antibody, e.g., brentuximab vedotin, as prior treatments. In further embodiments, an anti-CD30 antibody, e.g., brentuximab vedotin, was administered simultaneously with the autologous stem cell transplant. In some embodiments, the patient was first treated with an autologous stem cell transplant and then treated with an anti-CD30 antibody, e.g., brentuximab vedotin. In other embodiments, the patient was first treated with an anti-CD30 antibody, e.g., brentuximab vedotin and then treated with an autologous stem cell transplant. Brentuximab vedotin is also known as ADCETRIS®.

In particular embodiments, the at least one prior treatment failed. In embodiments, the subject failed to achieve a partial response after the at least one prior treatment. In other embodiments, the subject had a relapse after a complete response after the at least one prior treatment. In still other embodiments, the patient had progressive disease after a partial response or stable disease after the at least one prior treatment.

In other embodiments, the disclosure includes a method of treating a subject afflicted with a tumor derived from Hodgkin lymphoma wherein the subject has received at least one prior treatment for Hodgkin lymphoma selected from the group consisting of (i) an autologous stem cell therapy, (ii) an anti-CD30 antibody, e.g., brentuximab vedotin, and both (i) and (ii), comprising: (i) measuring a PD-L1 expression level on the tumor, wherein the tumor has a PD-L1 or PD-L2 expression level of at least 1%, and (ii) administering to the subject a therapeutically effective amount of an anti-PD-1 antibody or antigen-binding portion thereof or an anti-PD-L1 antibody or antigen-binding portion thereof.

In further embodiments, the disclosure includes a method for treating a subject afflicted with a tumor derived from a Hodgkin lymphoma comprising administering to the subject a therapeutically effective amount of an anti-PD-1 antibody or an antigen-binding portion thereof or an anti-PD-L1 antibody or antigen-binding portion thereof in combination with doxorubicin, vinblastine, and dacarbazine. In embodiments, the disclosure includes a method for treating a subject afflicted with a tumor derived from a Hodgkin lymphoma comprising administering to the subject a therapeutically effective amount of an anti-PD-1 antibody or an antigen-binding portion thereof or an anti-PD-L1 antibody or antigen-binding portion thereof in combination with doxorubicin, vinblastine, and dacarbazine, but not bleomycin.

In certain embodiments, the therapy of the present disclosure (e.g., administration of an anti-PD-1 antibody or an anti-PD-L1 antibody and, optionally, another anti-cancer agent) effectively increases the duration of survival of the subject. In some embodiments, the anti-PD-1 antibody therapy or anti-PD-L1 antibody therapy of the present disclosure increases the duration of survival of the subject in comparison to standard-of-care therapies (i.e., brentuximab vedotin or AVD chemotherapy). After the administration of an anti-PD-1 antibody or anti-PD-L1 antibody therapy, the subject having Hodgkin lymphoma tumor can exhibit an overall survival of at least about 10 months, at least about 11 months, at least about 12 months, at least about 13 months, at least about 14 months at least about 15 months, at least about 16 months, at least about 17 months, at least about 18 months, at least about 19 months, at least about 20 months, at least about 21 months, at least about 22 months, at least about 23 months, at least about 2 years, at least about 3 years, at least about 4 years, or at least about 5 years after the administration.

In other embodiments, the duration of survival or the overall survival of the subject is increased by at least about 1 month, at least about 2 months, at least about 3 months, at least about 4 months, at least about 5 months, at least about 6 months, at least about 7 months, at least about 8 months, at least about 9 months or at least about 1 year when compared to another subject treated with only a standard-of-care therapy (e.g., brentuximab vedotin or AVD chemotherapy). In some embodiments, the overall survival is increased by at least about 4 months, at least about 5 months, at least about 6 months, at least about 7 months, at least about 8 months, at least about 9 months, at least about 10 months, at least about 11 months, at least about 1 year, at least about 18 months, or at least about 2 years when the tumor is PD-L1 positive when compared to another subject treated with only a standard-of-care therapy (e.g., brentuximab vedotin or AVD chemotherapy). For example, the duration of survival or the overall survival of the subject is increased by at least about 5%, at least about 10%, at least about 15%, at least about 20%, at least about 25%, at least about 30%, at least about 40%, at least about 50%, or at least about 75% when compared to another subject treated with only a standard-of-care therapy (e.g., brentuximab vedotin or AVD chemotherapy).

In certain embodiments, the therapy of the present disclosure effectively increases the duration of progression free survival of the subject. For example, the progression free survival of the subject treated with a method of the disclosure is at least about 1 month, 2 months, 3 months, at least about 4 months, at least about 5 months, at least about 6 months, at least about 7 months, at least about 8 months, at least about 9 months, at least about 10 months, at least about 11 months, at least about 12 months, at least about 1 year, at least about eighteen months, at least about 2 years, at least about 3 years, at least about 4 years, or at least about 5 years.

In other embodiments, the subject is a human patient. In some embodiments, the subject has received another cancer therapy (e.g., brentuximab vedotin or chemotherapy), but is resistant or refractory to such another cancer therapy. In certain embodiments, the subject has a genetic alteration of the PD-1 ligand loci. In one embodiment, the subject has a 9p24.1 amplification. In other embodiments, the subject is PD-L1 positive. In some embodiments, the subject is PD-L2 positive.

The PD-L1 or PD-L2 status of a tumor (e.g., a tumor derived from HL) in a subject can be measured prior to administering any composition or utilizing any method disclosed herein. PD-L1 or PD-L2 expression can be determined by any methods known in the art.

In order to assess the PD-L1 and/or PD-L2 expression, in one embodiment, a test tissue sample can be obtained from the patient who is in need of the therapy. In another embodiment, the assessment of PD-L1 and/or PD-L2 expression can be achieved without obtaining a test tissue sample. In some embodiments, selecting a suitable patient includes (i) optionally providing a test tissue sample obtained from a patient with cancer of the tissue, the test tissue sample comprising tumor cells and/or tumor-infiltrating inflammatory cells; and (ii) assessing the proportion of cells in the test tissue sample that express PD-L1 and/or PD-L2 on the surface of the cells based on an assessment that the proportion of cells in the test tissue sample that express PD-L1 and/or PD-L2 on the cell surface is higher than a predetermined threshold level.

In any of the methods comprising the measurement of PD-L1 expression in a test tissue sample, however, it should be understood that the step comprising the provision of a test tissue sample obtained from a patient is an optional step. It should also be understood that in certain embodiments the "measuring" or "assessing" step to identify, or determine the number or proportion of, cells in the test tissue sample that express PD-L1 on the cell surface is performed by a transformative method of assaying for PD-L1 expression, for example by performing a reverse transcriptase-polymerase chain reaction (RT-PCR) assay or an IHC assay. In certain other embodiments, no transformative step is involved and PD-L1 expression is assessed by, for example, reviewing a report of test results from a laboratory. In certain embodiments, the steps of the methods up to, and including, assessing PD-L1 expression provides an intermediate result that may be provided to a physician or other healthcare provider for use in selecting a suitable candidate for the anti-PD-1 antibody or anti-PD-L1 antibody therapy. In certain embodiments, the steps that provide the intermediate result is performed by a medical practitioner or someone acting under the direction of a medical practitioner. In other embodiments, these steps are performed by an independent laboratory or by an independent person such as a laboratory technician.

In certain embodiments of any of the present methods, the proportion of cells that express PD-L1 is assessed by performing an assay to determine the presence of PD-L1 RNA. In further embodiments, the presence of PD-L1 RNA is determined by RT-PCR, in situ hybridization or RNase protection. In other embodiments, the proportion of cells that express PD-L1 is assessed by performing an assay to determine the presence of PD-L1 polypeptide. In further embodiments, the presence of PD-L1 polypeptide is determined by immunohistochemistry (IHC), enzyme-linked immunosorbent assay (ELISA), in vivo imaging, or flow cytometry. In some embodiments, PD-L1 expression is assayed by IHC. In other embodiments of all of these methods, cell surface expression of PD-L1 is assayed using, e.g., IHC or in vivo imaging. Chen et al., (2013) Clin Cancer Res 19(13): 3462-3473.

Imaging techniques have provided important tools in cancer research and treatment. Recent developments in molecular imaging systems, including positron emission tomography (PET), single-photon emission computed tomography (SPECT), fluorescence reflectance imaging (FRI), fluorescence-mediated tomography (FMT), bioluminescence imaging (BLI), laser-scanning confocal microscopy (LSCM) and multiphoton microscopy (MPM), will likely herald even greater use of these techniques in cancer research. Some of these molecular imaging systems allow clinicians to not only see where a tumor is located in the body, but also to visualize the expression and activity of specific molecules, cells, and biological processes that influence tumor behavior and/or responsiveness to therapeutic drugs (Condeelis and Weissleder, "In vivo imaging in cancer," *Cold Spring Harb. Perspect. Biol.* 2(12):a003848 (2010)). Antibody specificity, coupled with the sensitivity and resolution of PET, makes immunoPET imaging particularly attractive for monitoring and assaying expression of antigens in tissue samples (McCabe and Wu, "Positive progress in immunoPET—not just a coincidence," *Cancer Biother. Radiopharm.* 25(3):253-61 (2010); Olafsen et al., "ImmunoPET imaging of B-cell lymphoma using 124I-anti-CD20 scFv dimers (diabodies)," *Protein Eng. Des. Sel.* 23(4):243-9 (2010)). In certain embodiments of any of the present methods, PD-L1 expression is assayed by immunoPET imaging. In certain embodiments of any of the present methods, the proportion of cells in a test tissue sample that express PD-L1 is assessed by performing an assay to determine the presence of PD-L1 polypeptide on the surface of cells in the test tissue sample. In certain embodiments, the test tissue sample is a FFPE tissue sample. In other embodiments, the presence of PD-L1 polypeptide is determined by IHC assay. In further embodiments, the IHC assay is performed using an automated process. In some embodiments, the IHC assay is performed using an anti-PD-L1 monoclonal antibody to bind to the PD-L1 polypeptide.

In one embodiment of the present methods, an automated IHC method is used to assay the expression of PD-L1 on the surface of cells in FFPE tissue specimens. This disclosure provides methods for detecting the presence of human PD-L1 antigen in a test tissue sample, or quantifying the level of human PD-L1 antigen or the proportion of cells in the sample that express the antigen, which methods comprise contacting the test sample, and a negative control sample, with a monoclonal antibody that specifically binds to human PD-L1, under conditions that allow for formation of a complex between the antibody or portion thereof and human PD-L1. In certain embodiments, the test and control tissue samples are FFPE samples. The formation of a complex is then detected, wherein a difference in complex formation between the test sample and the negative control sample is indicative of the presence of human PD-L1 antigen in the sample. Various methods are used to quantify PD-L1 expression.

In a particular embodiment, the automated IHC method comprises: (a) deparaffinizing and rehydrating mounted tissue sections in an autostainer; (b) retrieving antigen using a decloaking chamber and pH 6 buffer, heated to 110° C. for 10 min; (c) setting up reagents on an autostainer; and (d) running the autostainer to include steps of neutralizing endogenous peroxidase in the tissue specimen; blocking non-specific protein-binding sites on the slides; incubating the slides with primary antibody; incubating with a post primary blocking agent; incubating with NovoLink Polymer; adding a chromogen substrate and developing; and counterstaining with hematoxylin.

For assessing PD-L1 expression in tumor tissue samples, a pathologist examines the number of membrane PD-L1+ tumor cells in each field under a microscope and mentally estimates the percentage of cells that are positive, then averages them to come to the final percentage. The different staining intensities are defined as 0/negative, 1+/weak, 2+/moderate, and 3+/strong. Typically, percentage values are first assigned to the 0 and 3+ buckets, and then the intermediate 1+ and 2+ intensities are considered. For highly heterogeneous tissues, the specimen is divided into zones, and each zone is scored separately and then combined into a single set of percentage values. The percentages of negative and positive cells for the different staining intensities are determined from each area and a median value is given to each zone. A final percentage value is given to the tissue for each staining intensity category: negative, 1+, 2+, and 3+. The sum of all staining intensities needs to be 100%. In one embodiment, the threshold number of cells that needs to be PD-L1 positive is at least about 100, at least about 125, at least about 150, at least about 175, or at least about 200 cells. In certain embodiments, the threshold number or cells that needs to be PD-L1 positive is at least about 100 cells.

Staining is also assessed in tumor-infiltrating inflammatory cells such as macrophages and lymphocytes. In most cases macrophages serve as an internal positive control since staining is observed in a large proportion of macrophages. While not required to stain with 3+ intensity, an absence of staining of macrophages should be taken into account to rule out any technical failure. Macrophages and lymphocytes are assessed for plasma membrane staining and only recorded for all samples as being positive or negative for each cell category. Staining is also characterized according to an outside/inside tumor immune cell designation. "Inside" means the immune cell is within the tumor tissue and/or on the boundaries of the tumor region without being physically intercalated among the tumor cells. "Outside" means that there is no physical association with the tumor, the immune cells being found in the periphery associated with connective or any associated adjacent tissue.

In certain embodiments of these scoring methods, the samples are scored by two pathologists operating independently, and the scores are subsequently consolidated. In certain other embodiments, the identification of positive and negative cells is scored using appropriate software.

A histoscore is used as a more quantitative measure of the IHC data. The histoscore is calculated as follows:

Histoscore=[(% tumor×1 (low intensity))+(% tumor×2 (medium intensity))+(% tumor×3 (high intensity))]

To determine the histoscore, the pathologist estimates the percentage of stained cells in each intensity category within a specimen. Because expression of most biomarkers is heterogeneous the histoscore is a truer representation of the overall expression. The final histoscore range is 0 (no expression) to 300 (maximum expression).

An alternative means of quantifying PD-L1 expression in a test tissue sample IHC is to determine the adjusted inflammation score (AIS) score defined as the density of inflammation multiplied by the percent PD-L1 expression by tumor-infiltrating inflammatory cells (Taube et al., "Colocalization of inflammatory response with B7-h1 expression in human melanocytic lesions supports an adaptive resistance mechanism of immune escape," *Sci. Transl. Med.* 4(127):127ra37 (2012)).

In one embodiment, the PD-L1 expression level of a tumor (e.g., a tumor derived from HL) is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100%. In another embodiment, the PD-L1 status of a tumor is at least about 1%. In other embodiments, the PD-L1 status of the subject is at least about 5%. In a certain embodiment, the PD-L1 status of a tumor is at least about 10%. In one embodiment, the PD-L1 status of the tumor is at least about 25%. In a particular embodiment, the PD-L1 status of the tumor is at least about 50%.

The present methods can treat any type of Hodgkin lymphoma (also referred to as Classical Hodgkin lymphoma). In certain embodiments, the Hodgkin lymphoma is cHL or nodular lymphocyte predominant type Hodgkin lymphoma. In certain embodiments, the Hodgkin lymphoma is a Hodgkin lymphoma selected from the group consisting of nodular sclerosing, mixed cellularity, lymphocyte rich, lymphocyte depleted, or lymphocyte-predominant. In certain embodiments, the subject has had an illness or been infected by the Epstein Barr virus (EBV).

The present methods can treat a Hodgkin lymphoma of any stage. There are at least four stages used for Hodgkin lymphoma: Stage I, Stage II, Stage III, and Stage IV. In Stage I, the cancer is limited to one lymph node region or a single organ. In Stage II, the cancer is in two lymph node regions or the cancer has invaded one organ and the nearby lymph nodes, but the cancer is still limited to a section of the body either above or below the diaphragm. In Stage III, the cancer has moved to lymph nodes both above and below the diaphragm, and the cancer may also be in one portion of tissue or an organ near the lymph nodes groups or in the spleen. In Stage IV, cancer cells are in several portions of one or more tissues. Stage IV Hodgkin lymphoma affects not only the lymph nodes but also other parts of the body, such as the liver, lungs or bones. Hodgkin lymphoma is also divided into the categories "A" and "B." A means that a subject doesn't have any significant symptoms as a result of the cancer. B indicates that a subject may have significant signs and symptoms, such as a persistent fever, unintended weight loss or severe night sweats.

Anti-PD-1 Antibodies and Anti-PD-L1 Antibodies

Anti-PD-1 antibodies suitable for use in the disclosed methods are antibodies that bind to PD-1 with high specificity and affinity, block the binding of PD-L1, and inhibit the immunosuppressive effect of the PD-1 signaling pathway. In any of the therapeutic methods disclosed herein, an anti-PD-1 or anti-PD-L1 "antibody" includes an antigen-binding portion that binds to the PD-1 or PD-L1 receptor, respectively, and exhibits the functional properties similar to those of whole antibodies in inhibiting ligand binding and upregulating the immune system. In certain embodiments, the anti-PD-1 antibody or antigen-binding portion thereof cross-competes with nivolumab for binding to human PD-1. In other embodiments, the anti-PD-L1 antibody or antigen-binding fragment thereof competes for binding with BMS-936559, MPDL3280A, MEDI4736, or MSB0010718C for binding to human PD-L1.

In other embodiments, the anti-PD-1 antibody or anti-PD-L1 antibody, or antigen-binding portions thereof is a chimeric, humanized, or human monoclonal antibody or a portion thereof. In certain embodiments for treating a human subject, the antibody is a humanized antibody. In other embodiments for treating a human subject, the antibody is a human antibody of an IgG1, IgG2, IgG3, or IgG4 isotype can be used.

In certain embodiments, the anti-PD-1 antibody, or anti-PD-L1 antibody, or antigen-binding portions thereof comprises a heavy chain constant region which is of a human IgG1 or IgG4 isotype. In certain other embodiments, the sequence of the IgG4 heavy chain constant region of the anti-PD-1 antibody or anti-PD-L1 antibody, or antigen-binding portions thereof, contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al., In vitro characterization of the anti-PD-1 antibody nivolumab, BMS-936558, and in vivo toxicology in non-human primates, *Cancer Imm Res*, 2(9):846-56 (2014)). In yet other embodiments, the antibody comprises a light chain constant region which is a human kappa or lambda constant region. In other embodiments, the anti-PD-1 antibody, or anti-PD-L1 antibody, or antigen-binding portions thereof is a monoclonal antibody or an antigen-binding portion thereof.

Human monoclonal antibodies that bind specifically to PD-1 with high affinity have been disclosed in U.S. Pat. No. 8,008,449. Other anti-PD-1 monoclonal antibodies have been described in, for example, U.S. Pat. Nos. 6,808,710, 7,488,802, 8,168,757, and 8,354,509, and PCT Publication No. WO 2012/145493. Each of the anti-PD-1 human monoclonal antibodies disclosed in U.S. Pat. No. 8,008,449 has been demonstrated to exhibit one or more of the following characteristics: (a) binds to human PD-1 with a $K_D$ of $1 \times 10^{-7}$ M or less, as determined by surface plasmon resonance using a Biacore biosensor system; (b) does not substantially bind to human CD28, CTLA-4 and/or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and (j) inhibits tumor cell growth in vivo. Anti-PD-1 antibodies usable in the present disclosure include monoclonal antibodies that bind specifically to human PD-1 and exhibit at least one, in some embodiments, at least five, of the preceding characteristics. In some embodiments, the anti-PD-1 antibody is nivolumab. In one embodiment, the anti-PD-1 antibody is pembrolizumab.

In one embodiment, the anti-PD-1 antibody is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., In vitro characterization of the anti-PD-1 antibody nivolumab, BMS-936558, and in vivo toxicology in non-human primates, *Cancer Imm Res,* 2(9): 846-56 (2014)). In another embodiment, the anti-PD-1 antibody or fragment thereof cross-competes with nivolumab. In other embodiments, the anti-PD-1 antibody or fragment thereof binds to the same epitope as nivolumab. In certain embodiments, the anti-PD-1 antibody has the same CDRs as nivolumab.

In another embodiment, the anti-PD-1 antibody (or antigen-binding portion thereof) cross-competes with pembrolizumab. In some embodiments, the anti-PD-1 antibody binds to the same epitope as pembrolizumab. In certain embodiments, the anti-PD-1 antibody has the same CDRs as pembrolizumab. In another embodiment, the anti-PD-1 antibody is pembrolizumab. Pembrolizumab (also known as "KEYTRUDA®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. Nos. 8,354,509 and 8,900,587; see also http://www.cancer.gov/drugdictionary?cdrid=695789 (last accessed: Dec. 14, 2014). Pembrolizumab has been approved by the FDA for the treatment of relapsed or refractory melanoma.

In other embodiments, the anti-PD-1 antibody (or antigen-binding portion thereof) cross-competes with MEDI0680. In still other embodiments, the anti-PD-1 antibody binds to the same epitope as MEDI0680. In certain embodiments, the anti-PD-1 antibody has the same CDRs as MEDI0680. In other embodiments, the anti-PD-1 antibody is MEDI0680 (formerly AMP-514), which is a monoclonal antibody. MEDI0680 is described, for example, in U.S. Pat. No. 8,609,089B2 or in http://www.cancer.gov/drugdictionary?cdrid=756047 (last accessed Dec. 14, 2014).

In certain embodiments, the first antibody is an anti-PD-1 antagonist. One example of the anti-PD-1 antagonist is AMP-224, which is a B7-DC Fc fusion protein. AMP-224 is discussed in U.S. Publ. No. 2013/0017199 or in http://www.cancer.gov/publications/dictionaries/cancer-drug?cdrid=700595 (last accessed Jul. 8, 2015).

In other embodiments, the anti-PD-1 antibody (or antigen-binding portion thereof) cross-competes with BGB-A317. In some embodiments, the anti-PD-1 antibody binds the same epitope as BGB-A317. In certain embodiments, the anti-PD-1 antibody has the same CDRs as BGB-A317. In certain embodiments, the anti-PD-1 antibody is BGB-A317, which is a humanized monoclonal antibody. BGB-A317 is described in U.S. Publ. No. 2015/0079109.

In other embodiments, the anti-PD-1 antibody (or antigen-binding portion thereof) cross-competes with INCSHR1210 (SHR-1210). In some embodiments, the anti-PD-1 antibody binds to the same epitope as INCSHR1210 (SHR-1210). In certain embodiments, the anti-PD-1 antibody has the same CDRs as INCSHR1210 (SHR-1210). In certain embodiments, the anti-PD-1 antibody is INCSHR1210 (SHR-1210), which is a human monoclonal antibody. INCSHR1210 (SHR-1210) is described in WO2015/085847.

In other embodiments, the anti-PD-1 antibody (or antigen-binding portion thereof) cross-competes with REGN-2810. In some embodiments, the anti-PD-1 antibody binds to the same epitope as REGN-2810. In certain embodiments, the anti-PD-1 antibody has the same CDRs as REGN-2810. In certain embodiments, the anti-PD-1 antibody is REGN-2810, which is a human monoclonal antibody. REGN-2810 is described in WO2015/112800.

In other embodiments, the anti-PD-1 antibody (or antigen-binding portion thereof) cross-competes with PDR001. In some embodiments, the anti-PD-1 antibody binds to the same epitope as PDR001. In certain embodiments, the anti-PD-1 antibody has the same CDRs as PDR001. In certain embodiments, the anti-PD-1 antibody is PDR001, which is a humanized monoclonal antibody. PDR001 is described in WO2015/112900.

In other embodiments, the anti-PD-1 antibody (or antigen-binding portion thereof) cross-competes with TSR-042 (ANB011). In some embodiments, the anti-PD-1 antibody binds to the same epitope as TSR-042 (ANB011). In certain embodiments, the anti-PD-1 antibody has the same CDRs as TSR-042 (ANB011). In certain embodiments, the anti-PD-1 antibody is TSR-042 (ANB011), which is a humanized monoclonal antibody. TSR-042 (ANB011) is described in WO2014/179664.

In other embodiments, the anti-PD-1 antibody (or antigen-binding portion thereof) cross-competes with STI-1110. In some embodiments, the anti-PD-1 antibody binds to the same epitope as STI-1110. In certain embodiments, the anti-PD-1 antibody has the same CDRs as STI-1110. In certain embodiments, the anti-PD-1 antibody is STI-1110, which is a human monoclonal antibody. STI-1110 is described in WO2014/194302.

Anti-PD-1 antibodies usable in the disclosed methods also include isolated antibodies that bind specifically to human PD-1 and cross-compete for binding to human PD-1 with nivolumab (see, e.g., U.S. Pat. Nos. 8,008,449 and 8,779,105; WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar to those of nivolumab by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 as, nivolumab are monoclonal antibodies. For administration to human subjects, these cross-competing antibodies are chimeric antibodies, or humanized or human antibodies. Such chimeric, humanized, or human monoclonal antibodies can be prepared and isolated by methods well known in the art.

Anti-PD-1 antibodies usable in the methods of the disclosed disclosure also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody; or any combination thereof.

Anti-PD-1 antibodies suitable for use in the disclosed compositions are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and upregulating the immune system. In certain embodiments, the anti-PD-1 antibody or antigen-binding portion thereof cross-competes with nivolumab for binding to human PD-1. In other embodiments, the anti-PD-1 antibody or antigen-binding portion thereof is a chimeric, humanized or human monoclonal antibody or a portion thereof. In certain embodiments, the antibody is a humanized antibody. In other embodiments, the antibody is a human antibody. Antibodies of an IgG1, IgG2, IgG3, or IgG4 isotype can be used.

In certain embodiments of any of the therapeutic methods described herein comprising administration of an anti-PD-1 antibody, the anti-PD-1 antibody is nivolumab. In other embodiments, the anti-PD-1 antibody is pembrolizumab. In other embodiments, the anti-PD-1 antibody is chosen from the human antibodies 17D8, 2D3, 4H1, 4A11, 7D3 and 5F4 described in U.S. Pat. No. 8,008,449. In still other embodiments, the anti-PD-1 antibody is MEDI0608 (formerly AMP-514), or AMP-224.

In certain embodiments, an anti-PD-1 antibody used in the methods can be replaced with another PD-1 or anti-PD-L1 antagonist. For example, because an anti-PD-L1 antibody prevents interaction between PD-1 and PD-L1, thereby exerting similar effects to the signaling pathway of PD-1, an anti-PD-L1 antibody can replace the use of an anti-PD-1 antibody in the methods disclosed herein. Therefore, in one embodiment, the present disclosure is directed to a method for treating a subject afflicted with a Hodgkin lymphoma comprising administering to the subject a therapeutically effective amount an anti-PD-L1 antibody. In certain embodiments, the anti-PD-L1 antibody is BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446 or atezolizumab) (see, e.g. Herbst et al. (2013) *J Clin Oncol* 31(suppl):3000. Abstract; U.S. Pat. No. 8,217,149), MEDI4736 (also called Durvalumab; Khleif (2013) In: Proceedings from the European Cancer Congress 2013; Sep. 27-Oct. 1, 2013; Amsterdam, The Netherlands. In other embodiments, the anti-PD-L1 antibody is CX-072 (also called CytomX; See WO2016/149201). In certain embodiments, the antibodies that cross-compete for binding to human PD-L1 with, or bind to the same epitope region of human PD-L1 as the above-references PD-L1 antibodies are monoclonal antibodies. For administration to human subjects, these cross-competing antibodies can be chimeric antibodies, or can be humanized or human antibodies. Such chimeric, humanized or human monoclonal antibodies can be prepared and isolated by methods well known in the art. Abstract 802, See U.S. Pat. No. 8,779,108 or US 2014/0356353, filed May 6, 2014), or MSB0010718C (also called Avelumab; See US 2014/0341917).

Because anti-PD-1 and anti-PD-L1 target the same signaling pathway and have been shown in clinical trials to exhibit similar levels of efficacy in a variety of cancers, (see Brahmer et al., (2012) *N Engl J Med* 366:2455-65; Topalian et al., (2012a) *N Engl J Med* 366:2443-54; WO 2013/173223), an anti-PD-L1 antibody can be substituted for the anti-PD-1 antibody in any of the therapeutic methods disclosed herein. In certain embodiments, the anti-PD-L1 antibody is BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446 or atezolizumab) (see, e.g., Herbst et al. (2013) *J Clin Oncol* 31(suppl):3000. Abstract; U.S. Pat. No. 8,217,149) or MEDI4736 (Khleif (2013) in: Proceedings from the European Cancer Congress 2013: Sep. 27-Oct. 1, 2013; Amsterdam, The Netherlands. Abstract 802). In certain embodiments, the antibodies that cross-compete for binding to human PD-L1 with, or bind to the same epitope region of human PD-L1 as the above-references PD-L1 antibodies are monoclonal antibodies. For administration to human subjects, these cross-competing antibodies can be chimeric antibodies, or can be humanized or human antibodies. Such chimeric, humanized, or human monoclonal antibodies can be prepared and isolated by methods well known in the art.

Combination Therapies with Anti-PD-1 or Anti-PD-L1 Antibodies

In certain embodiments, an anti-PD-1 antibody or anti-PD-L1 antibody is administered in combination with one or more other anti-cancer agents. In some embodiments, the anti-PD-1 antibody or anti-PD-L1 antibody is initially administered as a monotherapy for one or more doses, and is then administered in combination with an additional anti-cancer agent. In some embodiments, the other anti-cancer agent is any anti-cancer agent described herein or known in the art. In certain embodiments, the other anti-cancer agent is an anti-CTLA-4 antibody. In embodiments, the additional anti-cancer agent is a combination of doxorubicin, vinblastine, and dacarbazine. In one embodiment, the other anti-cancer agent is a chemotherapy or a platinum-based doublet chemotherapy (PT-DC). In other embodiments, the anti-cancer agent is a platinum agent (e.g., cisplatin, carboplatin), a mitotic inhibitor (e.g., paclitaxel, albumin-bound paclitaxel, docetaxel, taxotere, docecad), a fluorinated *Vinca* alkaloid (e.g., vinflunine, javlor), vinorelbine, vinblastine, etoposide, or pemetrexed gemcitabin.

In an embodiment, the other anti-cancer agent is Adcetris (Brentuximab Vedotin), Ambochlorin (Chlorambucil), Amboclorin (Chlorambucil), Becenum (Carmustine), BiCNU (Carmustine), Blenoxane (Bleomycin), Bleomycin, Brentuximab Vedotin, Carmubris (Carmustine), Carmustine, Chlorambucil, Clafen (Cyclophosphamide), Cyclophosphamide, Cytoxan (Cyclophosphamide), Dacarbazine, Doxorubicin Hydrochloride, DTIC-Dome (Dacarbazine), Leukeran (Chlorambucil), Linfolizin (Chlorambucil), Lomustine, Matulane (Procarbazine Hydrochloride), Mechlorethamine Hydrochloride, Mustargen (Mechlorethamine Hydrochloride), Neosar (Cyclophosphamide), Prednisone, Procarbazine Hydrochloride, Velban (Vinblastine Sulfate), Velsar (Vinblastine Sulfate), Vinblastine Sulfate, Vincasar PFS (Vincristine Sulfate), and/or Vincristine Sulfate. In other embodiments, the other anti-cancer agent is any combination of drugs from ABVD, ABVE, ABVE-PC, BEACOPP, COPDAC, COPP, COPP-ABV, ICE, MOPP, OEPA, OPPA, STANFORD V, and/or VAMP. (See http://www.cancer.gov/about-cancer/treatment/drugs/hodgkin-lymphoma, last visited May 27, 2016).

In a particular embodiment, the anti-cancer agents to be administered in combination with an anti-PD-1 antibody or an anti-PD-L1 antibody are doxorubicin, vinblastine, and dacarbazine. In other embodiments, the anti-cancer agents to be administered in combination with an anti-PD-1 antibody or an anti-PD-L1 antibody are doxorubicin, vinblastine, and dacarbazine, but not including bleomycin.

In certain embodiments, the other anti-cancer agent is any other anti-cancer agent known in the art. In some embodiments, two or more additional anti-cancer agents are administered in combination with the anti-PD-1 or anti-PD-L1 antibody. In some embodiments, the PD-1 or PD-L1 antibody is combined with surgical resection, radiation therapy, and/or a step cell transplant.

In certain embodiments, the anti-PD-1 antibody or anti-PD-L1 antibody can be combined with another immunotherapy. In certain embodiments, immunotherapy involving blockade of immune checkpoints is administered as a monotherapy. In other embodiments, immunotherapy involving blockade of immune checkpoints is administered in combination with other therapies. In some embodiments, Hodgkin lymphoma patients can benefit from the combination of different immunotherapeutic drugs.

Anti-CTLA-4 Antibodies

In certain embodiments, an anti-PD-1 antibody or anti-PD-L1 antibody is combined with an anti-CTLA-4 antibody. Anti-CTLA-4 antibodies useful for the instant combination can bind to human CTLA-4 so as to disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing or prolonging an immune response.

Human monoclonal antibodies that bind specifically to CTLA-4 with high affinity have been disclosed in U.S. Pat. Nos. 6,984,720 and 7,605,238. Other anti-CTLA-4 monoclonal antibodies have been described in, for example, U.S. Pat. Nos. 5,977,318, 6,051,227, 6,682,736, and 7,034,121. The anti-CTLA-4 human monoclonal antibodies disclosed in U.S. Pat. Nos. 6,984,720 and 7,605,238 have been demonstrated to exhibit one or more of the following characteristics: (a) binds specifically to human CTLA-4 with a binding affinity reflected by an equilibrium association constant ($K_a$) of at least about $10^7$ $M^{-1}$, or about $10^9$ $M^{-1}$, or about $10^{10}$ $M^{-1}$ to $10^{11}$ $M^{-1}$ or higher, as determined by Biacore analysis; (b) a kinetic association constant ($k_a$) of at least about $10^3$, about $10^4$, or about $10^5$ $m^{-1}$ $s^{-1}$; (c) a kinetic disassociation constant ($k_d$) of at least about $10^3$, about $10^4$, or about $10^5$ $m^{-1}$ $s^{-1}$; and (d) inhibits the binding of CTLA-4 to B7-1 (CD80) and B7-2 (CD86). Anti-CTLA-4 antibodies usable in the present disclosure include monoclonal antibodies that bind specifically to human CTLA-4 and exhibit at least one, at least two or, in one embodiment, at least three of the preceding characteristics. An exemplary clinical anti-CTLA-4 antibody is the human monoclonal antibody 10D1 (now known as ipilimumab and marketed as YERVOY®) as disclosed in U.S. Pat. No. 6,984,720. Ipilimumab is an anti-CTLA-4 antibody for use in the methods disclosed herein. Another anti-CTLA-4 antibody usable in the present methods is tremelimumab.

An exemplary clinical anti-CTLA-4 antibody useful for the combination is the human monoclonal antibody 10D1 (now known as ipilimumab and marketed as YERVOY®) as disclosed in U.S. Pat. No. 6,984,720. Ipilimumab is an anti-CTLA-4 antibody for use in the methods disclosed herein. Ipilimumab is a fully human, IgG1 monoclonal antibody that blocks the binding of CTLA-4 to its B7 ligands, thereby stimulating T cell activation and improving overall survival (OS) in patients with advanced melanoma.

Another anti-CTLA-4 antibody useful for the present methods is tremelimumab (also known as CP-675,206). Tremelimumab is human IgG2 monoclonal anti-CTLA-4 antibody. Tremelimumab is described in WO/2012/122444, U.S. Publ. No. 2012/263677, or WO Publ. No. 2007/113648 A2.

Anti-CTLA-4 antibodies usable in the disclosed methods also include isolated antibodies that bind specifically to human PD-1 and cross-compete for binding to human CTLA-4 with ipilimumab or tremelimumab or bind to the same epitope region of human CTLA-4 as ipilimumab or tremelimumab. In certain embodiments, the antibodies that cross-compete for binding to human CTLA-4 with, or bind to the same epitope region of human PD-1 as does ipilimumab or tremelimumab, are antibodies comprising a heavy chain of the human IgG1 isotype. For administration to human subjects, these cross-competing antibodies are chimeric antibodies, or humanized or human antibodies. Usable anti-CTLA-4 antibodies also include antigen-binding portions of the above antibodies such as Fab, $F(ab')_2$, Fd, or Fv fragments.

Ipilimumab (YERVOY®) is a fully human, IgG1 monoclonal antibody that blocks the binding of CTLA-4 to its B7 ligands, thereby stimulating T cell activation and improving overall survival (OS) in patients with advanced melanoma (Hodi et al., (2010) *N Engl J Med* 363:711-23). Concurrent therapy with nivolumab and ipilimumab in a Phase 1 clinical trial produced rapid and deep tumor regression in a substantial proportion of patients with advanced melanoma, and was significantly more effective than either antibody alone (Wolchok et al., (2013) *N Engl J Med* 369(2):122-33; WO 2013/173223).

Chemotherapy

In some embodiments, the anti-PD-1 antibody is administered in combination with any chemotherapy known in the art. In embodiments, the anti-PD-1 antibody is administered in combination with doxorubicin, vinblastine, and dacarbazine. In embodiments, the combination of doxorubicin, vinblastine, and dacarbazine is administered once about every one, two, three or four weeks. In embodiments, doxorubicin is administered at a dose of about 10 mg/m²-about 40 mg/m², about 10 mg/m²-about 30 mg/m², or about 20 mg/m²-about 30 mg/m². In other embodiments, vinblastine is administered at a dose of about 0.1 mg/m² to about 10 mg/m², about 1 mg/m² to about 10 mg/m², or about 5 mg/m² to about 10 mg/m². In some embodiments, dacarbazine is administered at a dose of about 200 mg/m²-about 500 mg/m², about 250 mg/m² to about 500 mg/m², or about 300 mg/m²-about 400 mg/m². In some embodiments, doxorubicin is administered at a dose of about 10 mg/m², about 15 mg/m², about 20 mg/m², about 25 mg/m², about 30 mg/m², about 35 mg/m², about 40 mg/m², about 45 mg/m², or about 50 mg/m². In certain embodiments, vinblastine is administered at a dose of about 0.1 mg/m$^2$, about 1 mg/m$^2$, about 2 mg/m$^2$, about 3 mg/m$^2$, about 4 mg/m$^2$, about 5 mg/m$^2$, about 6 mg/m$^2$, about 7 mg/m$^2$, about 8 mg/m$^2$, about 9 mg/m$^2$, about 10 mg/m$^2$, about 11 mg/m$^2$, about 12 mg/m$^2$, about 13 mg/m$^2$, about 14 mg/m$^2$, about 15 mg/m$^2$, or about 20 mg/m$^2$. In some embodiments, dacarbazine is administered at a dose of about 200 mg/m$^2$, about 225 mg/m$^2$, about 250 mg/m$^2$, about 275 mg/m$^2$, about 300 mg/m$^2$, about 325 mg/m$^2$, about 350 mg/m$^2$, about 375 mg/m$^2$, about 400 mg/m$^2$, about 425 mg/m$^2$, about 450 mg/m$^2$, about 475 mg/m$^2$, or about 500 mg/m$^2$. In further embodiments, doxorubicin is administered at a dose of 25 mg/m$^2$, vinblastine is administered at a dose of 6 mg/m$^2$, and dacarbazine is administered at a dose of 375 mg/m$^2$ once about every 2 weeks. In still further embodiments, the subject is not administered bleomycin.

In certain embodiments, the chemotherapy is a platinum based-chemotherapy. Platinum-based chemotherapies are coordination complexes of platinum. In some embodiments, the platinum-based chemotherapy is a platinum-doublet chemotherapy. In one embodiment, the chemotherapy is administered at the approved dose for the particular indication. In other embodiments, the chemotherapy is administered at any dose disclosed herein. In some embodiments, the platinum-based chemotherapy is cisplatin, carboplatin, oxaliplatin, satraplatin, picoplatin, nedaplatin, triplatin, lipoplatin, or combinations thereof. In certain embodiments, the platinum-based chemotherapy is any other platinum-based chemotherapy known in the art. In some embodiments, the chemotherapy is the nucleotide analog gemcitabine. In an embodiment, the chemotherapy is a folate antimetabolite. In an embodiment, the folate antimetabolite is pemetrexed. In certain embodiments the chemotherapy is a taxane. In other embodiments, the taxane is paclitaxel. In other embodiments, the chemotherapy is a nucleoside analog. In one embodiment, the nucleoside analog is gemcitabine. In some embodiments, the chemotherapy is any other chemotherapy known in the art. In certain embodiments, at least one, at least two or more chemotherapeutic agents are administered in combination with the anti-PD-1 antibody. In some embodiments, the anti-PD-1 antibody is administered in combination with gemcitabine and cisplatin. In some embodiments, the anti-PD-1 antibody is administered in combination with pemetrexed and cisplatin. In certain embodiments, the anti-PD-1 antibody is administered in combination with gemcitabine and pemetrexed. In one embodiment, the anti-PD-1 antibody is administered in combination with paclitaxel and carboplatin. In an embodiment, an anti-CTLA-4 antibody is additionally administered.

Pharmaceutical Compositions and Dosages

Therapeutic agents of the present disclosure can be constituted in a composition, e.g., a pharmaceutical composition containing an antibody and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. In one embodiment, the carrier for a composition containing an antibody is suitable for intravenous, intramuscular, subcutaneous, parenteral, spinal or epidermal administration (e.g., by injection or infusion), whereas the carrier for some compositions is suitable for non-parenteral, e.g., oral, administration. A pharmaceutical composition of the disclosure can include one or more pharmaceutically acceptable salts, anti-oxidant, aqueous and non-aqueous carriers, and/or adjuvants such as preservatives, wetting agents, emulsifying agents and dispersing agents.

Dosage regimens are adjusted to provide the optimum desired response, e.g., a maximal therapeutic response and/or minimal adverse effects. In some embodiments, the anti-PD-1 antibody or antigen binding portion thereof is administered at a weight-based dose. For administration of an anti-PD-1 antibody at a weight-based dose, as a monotherapy or in combination with another anti-cancer agent, the dosage can range from about 0.01 mg/kg to about 20 mg/kg, about 0.1 mg/kg to about 10 mg/kg, about 0.1 mg/kg to about 5 mg/kg, about 1 mg/kg to about 5 mg/kg, about 2 mg/kg to about 5 mg/kg, about 7.5 mg/kg to about 12.5 mg/kg, or about 0.1 mg/kg to about 30 mg/kg of the subject's body weight. For example, dosages can be about 0.1 mg/kg, about 0.3 mg/kg, about 1 mg/kg, about 2 mg/kg, about 3 mg/kg, about 5 mg/kg, or about 10 mg/kg body weight, or about 0.3 mg/kg, about 1 mg/kg, about 2 mg/kg, about 3 mg/kg, or about 5 mg/kg body weight. The dosing schedule is typically designed to achieve exposures that result in sustained receptor occupancy (RO) based on typical pharmacokinetic properties of an antibody. An exemplary treatment regime entails administration about once per week, once about every 2 weeks, once about every 3 weeks, once about every 4 weeks, once about a month, once about every 3-6 months or longer. In certain embodiments, an anti-PD-1 antibody such as nivolumab is administered to the subject once about every 2 weeks. In other embodiments, the antibody is administered once about every 3 weeks. The dosage and scheduling can change during a course of treatment. For example, a dosing schedule for anti-PD-1 monotherapy can comprise administering the antibody: (i) about every 2 weeks in about 6-week cycles; (ii) about every 4 weeks for about six dosages, then about every three months; (iii) about every 3 weeks; (iv) about 3 mg/kg to about 10 mg/kg once followed by about 1 mg/kg every about 2-3 weeks. Considering that an IgG4 antibody typically has a half-life of 2-3 weeks, a dosage regimen for an anti-PD-1 antibody of the disclosure comprises at least about 0.3 mg/kg to at least about 10 mg/kg body weight, at least about 1 mg/kg to at least about 5 mg/kg body weight, or at least about 1 mg/kg to at least about 3 mg/kg body weight via intravenous administration, with the antibody being given every about 14-21 days in up to about 6-week or about 12-week cycles until complete response or confirmed progressive disease. In certain embodiments, an anti-PD-1 monotherapy is administered at 3 mg/kg every 2 weeks until progressive disease or unacceptable toxicity. In some embodiments, the antibody treatment, or any combination treatment disclosed herein, is continued for at least about 1 month, at least about 3 months, at least about 6 months, at least about 9 months, at least about 1 year, at least about 18 months, at least about 24 months, at least about 3 years, at least about 5 years, or at least about 10 years.

When used in combinations with other cancer agents, the dosage of an anti-PD-1 antibody can be lowered compared to the monotherapy dose. Dosages of nivolumab that are lower than the typical 3 mg/kg, but not less than 0.001 mg/kg, are subtherapeutic dosages. The subtherapeutic doses of an anti-PD-1 antibody used in the methods herein are higher than 0.001 mg/kg and lower than 3 mg/kg. In some embodiments, a subtherapeutic dose is about 0.001 mg/kg to about 1 mg/kg, about 0.01 mg/kg to about 1 mg/kg, about 0.1 mg/kg to about 1 mg/kg, or about 0.001 mg/kg to about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%). In some embodiments, 0.3 mg/kg dosing can allow for sufficient exposure to lead to maximal biologic activity. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%) (Brahmer et al., (2010) *J Clin Oncol* 28:3167-75). Thus, 0.3 mg/kg dosing can allow for sufficient exposure to lead to maximal biologic activity.

Although higher nivolumab monotherapy dosing up to about 10 mg/kg every two weeks has been achieved without reaching the maximum tolerated dose (MTD), the significant toxicities reported in other trials of checkpoint inhibitors plus anti-angiogenic therapy (see, e.g., Johnson et al. (2013) *Cancer Immunol Res* 1:373-77; Rini et al. (2011) *Cancer* 117:758-67) support the selection of a nivolumab dose lower than 10 mg/kg.

In certain embodiments, the dose of an anti-PD-1 antibody (or an anti-PD-L1 antibody) is a fixed dose in a pharmaceutical composition. In other embodiments, the method of the present disclosure can be used with a flat dose (a dose given to a patient irrespective of the body weight of the patient). In embodiments, the flat dose of the anti-PD-1 antibody or antigen binding portion thereof is at least about 100 mg, 120 mg, 140 mg, 160 mg, 180 mg, 200 mg, 220 mg, 240 mg, 260 mg, 280 mg, 300 mg, 400 mg, 420 mg, 440 mg, 460 mg, 480 mg, 500 mg, 520 mg, 540 mg, 560 mg, or 600 mg. For example, a flat dose of a nivolumab can be about 240 mg. For example, a flat dose of pembrolizumab can be about 200 mg. In embodiments, the anti-PD-1 antibody or antigen-binding portion thereof is administered at a dose of about 240 mg. In embodiments, the anti-PD-1 antibody or antigen-binding portion thereof is administered at a dose of about 360 mg. In embodiments, the anti-PD-1 antibody or antigen-binding portion thereof is administered at a dose of about 480 mg. In embodiments, the flat dose of the anti-PD-1 antibody or antigen binding portion thereof is administered once about every week, every two weeks, every three weeks, every four weeks, every five weeks, or every six weeks. In one embodiment, 360 mg of the anti-PD-1 antibody or antigen binding fragment is administered once every 3 weeks. In another embodiment, 480 mg of the anti-PD-1 antibody or antigen binding fragment is administered once every 4 weeks.

Ipilimumab (YERVOY®) is approved for the treatment of melanoma at 3 mg/kg given intravenously once every 3 weeks for 4 doses. Thus, in some embodiments, about 3 mg/kg is the highest dosage of ipilimumab used in combination with the anti-PD-1 antibody though, in certain embodiments, an anti-CTLA-4 antibody such as ipilimumab can be dosed within the range of about 0.3 mg/kg to about 10 mg/kg, about 0.5 mg/kg to about 10 mg/kg, about 0.5 mg/kg to about 5 mg/kg, or about 1 mg/kg to about 5 mg/kg body weight about every two or three weeks when combined with nivolumab. In other embodiments, ipilimumab is administered on a different dosage schedule from nivolumab. In some embodiments, ipilimumab is administered about every week, about every two weeks, about every three weeks, about every 4 weeks, about every five weeks, about every six weeks, about every seven weeks, about every eight weeks, about every nine weeks, about every ten weeks, about every eleven weeks, about every twelve weeks or about every fifteen weeks. Dosages of ipilimumab that are lower than the typical 3 mg/kg every 3 weeks, but not less than 0.001 mg/kg, are subtherapeutic dosages. The doses of an anti-CTLA-4 antibody used in the methods herein are higher than 0.001 mg/kg and lower than 3 mg/kg. In some embodiments, a dose of an anti-CTLA-4 antibody is about 0.001 mg/kg-about 1 mg/kg, about 0.01 mg/kg to about 1 mg/kg, about 0.1 mg/kg to about 1 mg/kg, or about 0.001 mg/kg to about 0.1 mg/kg body weight. In some embodiments, the dose of an anti-CTLA-4 antibody is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. In some embodiments, although nivolumab is tolerated up to 10 mg/kg given intravenously every 2 weeks, doses of the anti-PD-1 antibody do not exceed about 3 mg/kg when combined with ipilimumab. In certain embodiments, based on risk-benefit and PK-PD assessments, the dosage useful for the disclosed methods comprises a combination of nivolumab at about 1 mg/kg plus ipilimumab at about 3 mg/kg, nivolumab at about 3 mg/kg plus ipilimumab at about 1 mg/kg, or nivolumab at about 3 mg/kg plus ipilimumab at about 3 mg/kg, each administered at a dosing frequency of once about every 2-4 weeks, in certain embodiments, once about every 2 weeks or once about every 3 weeks. In certain other embodiments, nivolumab is administered at a dosage of about 0.1 mg/kg, about 0.3 mg/kg, about 1 mg/kg, about 2 mg/kg, about 3 mg/kg or about 5 mg/kg in combination with ipilimumab administered at a dosage of about 0.1 mg/kg, about 0.3 mg/kg, about 1 mg/kg, about 2 mg/kg, about 3 mg/kg or about 5 mg/kg, once about every 2 weeks, once about every 3 weeks, or once about every 4 weeks.

In certain embodiments, the combination of an anti-PD-1 antibody and an anti-CTLA-4 antibody is administered intravenously to the subject in an induction phase about every 2 or 3 weeks for 1, 2, 3, or 4 administrations. In certain embodiments, the combination of nivolumab and ipilimumab is administered intravenously in the induction phase about every 2 weeks or about every 3 weeks for about 4 administrations. The induction phase is followed by a maintenance phase during which only the anti-PD-1 antibody is administered to the subject at a dosage of about 0.1 mg/kg, about 0.3 mg/kg, about 1 mg/kg, about 2 mg/kg, about 3 mg/kg, about 5 mg/kg, or about 10 mg/kg about every two or three weeks for as long as the treatment proves efficacious or until unmanageable toxicity or disease progression occurs. In certain embodiments, nivolumab is administered during the maintenance phase at a dose of about 3 mg/kg body about every 2 weeks.

In certain embodiments, the anti-PD-1 antibody and the anti-CTLA-4 antibody is formulated as a single composition, wherein the dose of the anti-PD-1 antibody and the dose of the anti-CTLA-4 antibody are combined in a fixed-dose at a ratio of 1:50, 1:40, 1:30, 1:20, 1:10. 1:5, 1:3, 1:1, 3:1, 5:1, 10:1, 20:1, 30:1, 40:1, or 50:1. In certain embodiments, the dose of the anti-CTLA-4 antibody is a flat dose, which is given to a patient irrespective of the body weight. In some embodiments, the flat dose of the anti-CTLA-4 antibody is at least about 40 mg, 50 mg, 60 mg, 70 mg, 80 mg, 90 mg, 100 mg, 120 mg, 140 mg, 160 mg, 180 mg, or 200 mg. In a specific embodiment, the flat dose of the anti-CTLA-4 antibody is about 80 mg.

For combination of nivolumab with other anti-cancer agents, these agents are administered at their approved dosages. Treatment is continued as long as clinical benefit is observed or until unacceptable toxicity or disease progression occurs. Nevertheless, in certain embodiments, the dosages of these anti-cancer agents administered are significantly lower than the approved dosage, i.e., a subtherapeutic dosage, of the agent is administered in combination with the anti-PD-1 antibody. The anti-PD-1 antibody can be administered at the dosage that has been shown to produce the highest efficacy as monotherapy in clinical trials, e.g., about 3 mg/kg of nivolumab administered once about every three weeks (Topalian et al., (2012a) *N Engl J Med* 366:2443-54; Topalian et al., (2012b) *Curr Opin Immunol* 24:207-12), or at a significantly lower dose, i.e., at a subtherapeutic dose. In certain embodiments, the anti-PD-1 antibody is administered at about 3 mg/kg once about every two weeks.

Dosage and frequency vary depending on the half-life of the antibody in the subject. In general, human antibodies show the longest half-life, followed by humanized antibodies, chimeric antibodies, and non-human antibodies. The dosage and frequency of administration can vary depending on whether the treatment is prophylactic or therapeutic. In prophylactic applications, a relatively low dosage is typically administered at relatively infrequent intervals over a long period of time. Some patients continue to receive treatment for the rest of their lives. In therapeutic applications, a relatively high dosage at relatively short intervals is sometimes required until progression of the disease is reduced or terminated, or until the patient shows partial or complete amelioration of symptoms of disease. Thereafter, the patient can be administered a prophylactic regime.

Actual dosage levels of the active ingredient or ingredients in the pharmaceutical compositions of the present disclosure can be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present disclosure employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present disclosure can be administered via one or more routes of administration using one or more of a variety of methods well known in the art. As will be appreciated by the skilled artisan, the route and/or mode of administration will vary depending upon the desired results.

Kits

Also within the scope of the present disclosure are kits comprising an anti-PD-1 antibody and, optionally, another anti-cancer agent for therapeutic uses. Kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with a Hodgkin lymphoma, the kit comprising: (a) any dosage described herein of an anti-cancer agent which is an antibody or an antigen-binding portion thereof that specifically binds to the PD-1 receptor and inhibits PD-1 activity; and, optionally, (b) instructions for using the anti-PD-1 antibody and in any of the therapy methods disclosed herein. In some embodiments, the kit contains, optionally, another anti-cancer agent(s) (e.g., doxorubicin, vinblastine, and dacarbazine) and instructions for the use of that agent. In certain embodiments, the kit comprises additional step between (a) and (b): instructions for determining the PD-L1 and/or PD-L2 expression of the tumor. In some embodiments, the kit comprises an agent to determine the PD-L1 and/or PD-L2 expression of the tumor. In one embodiment, the PD-L1 and/or PD-L2 expression is measured by an anti-PD-L1 and/or PD-L2 antibody or antigen-binding portion thereof.

The present disclosure is further illustrated by the following example, which should not be construed as further limiting. The contents of all references cited throughout this application are expressly incorporated herein by reference.

Cross-reference to earlier filed applications: the present application claims benefit to U.S. provisional application No. 62/344,880 filed Jun. 2, 2017, which is incorporated by reference herein by reference in its entirety.

EXAMPLES

Example 1

Treatment of cHL with Nivolumab Monotherapy after Failure of Autologous Stem Cell Transplantation (ASCT) and Subsequent Brentuximab Vedotin In a phase 2 study, the efficacy and safety of nivolumab monotherapy in patients with cHL after failure of ASCT and subsequent brentuximab vedotin was determined. The primary endpoint of the study included the objective response rate (ORR) as assessed by the Independent Radiologic Review Committee (IRRC). The secondary endpoints included 1) IRRC-assessed complete remission (CR), partial remission (PR), and duration of response (DOR); 2) investigator-assessed ORR and DOR; 3) safety; and 4) quality of life (QoL).

Methods

Study Design

The study was part of an ongoing, multicenter-noncomparative, multicohort, phase 2 registrational study in patients with cHL from 34 study centers across Europe, Canada, and the US.

As shown in FIG. 1, key inclusion criteria included 1) prior treatment with ASCT followed by brentuximab vedotin; and 2) (i) failure to achieve greater than PR after the most recent treatment, (ii) relapse after CR, or (iii) progressive disease (PD) after PR or stable disease (SD).

Patients meeting the above inclusion criteria received nivolumab every 2 weeks at a dosage of 3 mg/kg. Treatment continued until disease progression or unacceptable toxicity occurred. At any time, patients had the option to elect to discontinue nivolumab treatment and proceed to hematopoietic stem cell transplantation (SCT). (See FIG. 1).

Assessment

Patients were assessed for efficacy, safety, and quality of life (QoL) associated with nivolumab treatment.

Efficacy was determined by assessing tumor response per 2007 IWG criteria. During the first year, tumor response was measured using CT or MRI at baseline and at Weeks 9, 17, 25, 37, and 49. Afterwards, tumor response was measured every 16 weeks until Week 97. After Week 97, the response was measured every 26 weeks. FDG-PET scan was also performed at baseline and Weeks 17 and 25.

Safety was determined by assessing all adverse events (AEs) that occurred as a result of the treatment. AEs were categorized based on their severity and included: fatigue, infusion-related reaction, rash, pyrexia, arthralgia, nausea, diarrhea, pruritus, and pneumonitis. (See Table 4).

Quality of life was determined using the EQ-5D and European Organization for Research and Treatment of Cancer Quality-of-Life Questionnaire-Core 30 (EORTC QLQ-C30).

Statistical Analysis

The initial planned sample size of the study was 60 patients, which would provide approximately 93% power to reject the null hypothesis that the ORR is ≤20%, assuming an ORR of 40% and given a 2-sided alpha of 5%. However, 80 patients were enrolled due to high demand from investigators and also to account for the possibility of a high rate of screening failures.

Time-to-response assessments were summarized using the Kaplan-Meier method.

Results

Patients

A total of 80 patients with cHL were enrolled and received nivolumab treatment. The baseline characteristics of the enrolled patients are provided in Table 2. At database lock, 51 of the 80 patients (64%) remained on nivolumab treatment. The median number of doses received was 17 (range of 3-25). Among the 29 patients who discontinued the nivolumab treatment, primary reasons for the discontinuation included: disease progression (n=13) and SCT (allogeneic SCT, n=5; autologous SCT, n=1). At time of the transplantation, the best responses were CR (n=1), PR (n=3), and SD (n=2). All patients were alive at data cut-off.

TABLE 2

Patient characteristics at baseline (N = 80)

| Characteristics | Value |
| --- | --- |
| Age (years), median (range) | 37 (18-72) |
| Age <65 years | 77 (96) |
| Male sex | 51 (64) |
| Previous lines of therapy, [a]median (range) | 4 (3-15) |
| ≥5 lines of therapy | 39 (49) |
| Previous radiation therapy | 59 (74) |
| Previous ASCT | 80 (100) |
| 1 | 74 (93) |
| ≥2 | 6 (8) |

Data shown as n (%) unless indicated otherwise
[a]Excluding high-dose preparative regimen prior to ASCT Efficacy Objective Response Rate (ORR)

The ORR as assessed by the IRRC and investigators are provided in Table 3. The median time to first objective response was 2.1 months (range 1.6-5.7 months). As assessed by the IRRC, 53 of the 80 patients (66%) had reduction in tumor burden, with 7 patients having complete remission. Under investigator assessment, 58 patients (73%) showed reduced tumor burden and of those patients, 22 patients had complete remission. This discordance in complete remission was largely based on FDG-PET scan interpretation and was not considered to meaningfully impact clinical activity interpretation, as 13/19 investigator assessed complete remission were assessed at least as partial remission by the IRRC. IRRC ORR was 72% in patients (n=43) with no prior response to their most recent brentuximab vedotin.

TABLE 3

ORR as assessed by IRRC and investigators

|  | IRRC (n = 80) | Investigator (n = 80) |
| --- | --- | --- |
| ORR, 95% CI | 53 (66); 55-76 | 58 (73); 61-82 |
| Best overall response |  |  |
| Complete remission | 7 (9) | 22 (28) |
| Partial remission | 46 (58) | 36 (45) |
| Stable disease | 18 (23) | 18 (23) |
| Progressive disease | 6 (8) | 3 (4) |
| Unable to determine | 3 (4)[a] | 1 (1)[b] |

Data shown as n (%) unless indicated otherwise
[a]No post-baseline tumor assessment available before or on the day of subsequent therapy (if any) or assessment not available
[b]No radiographic assessment after the first dose Duration of Response (DOR)

After a median follow-up of 8.9 months, the median DOR was 7.8 months (95% CI 6.6—not estimable (NE)).

Response Characteristics and Change in Target Lesion

Figure 2A:
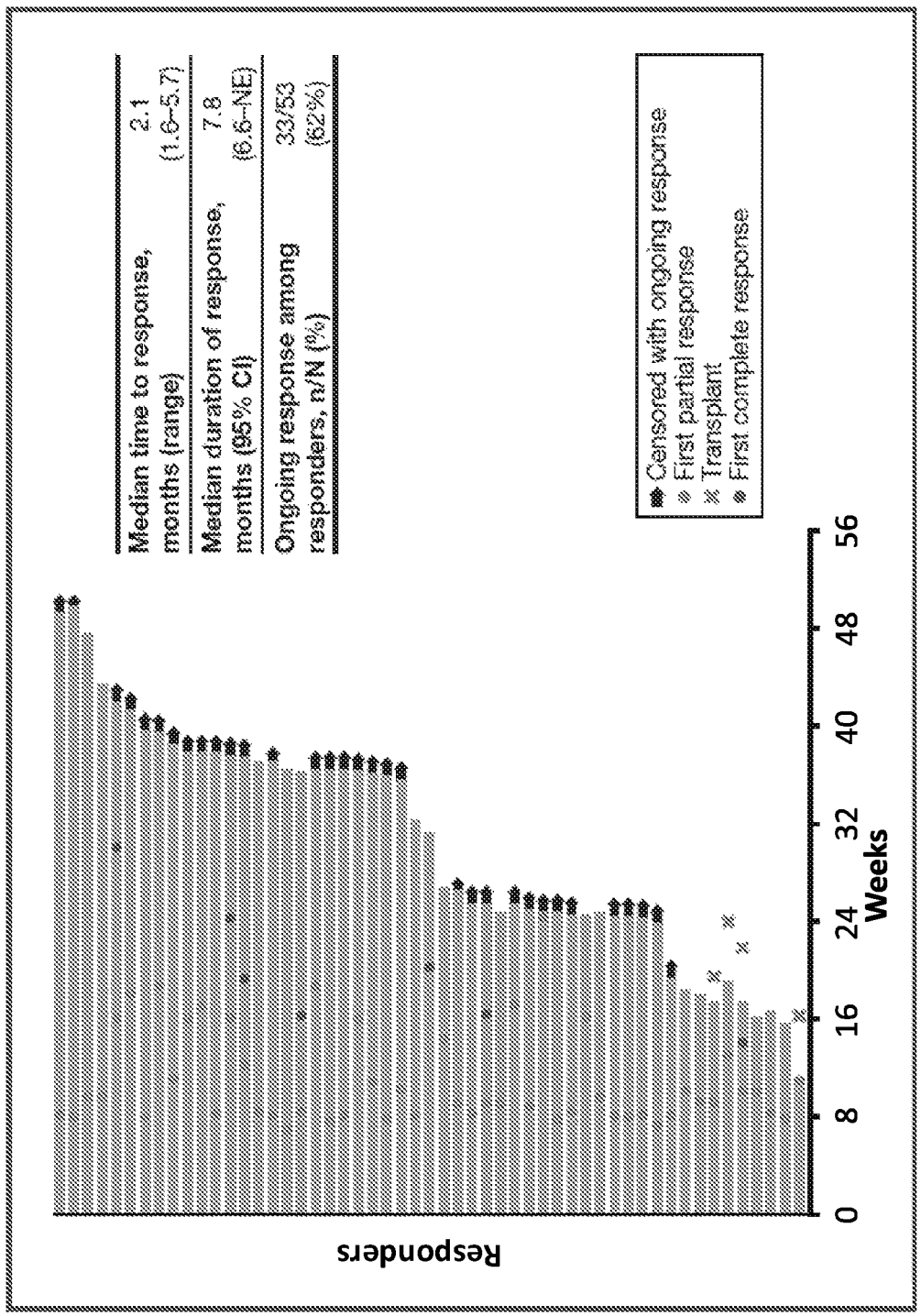
FIGS. 2A-2C show a summary of the response and the change in tumor burden in cHL patients after nivolumab monotherapy.
Figure 2B:
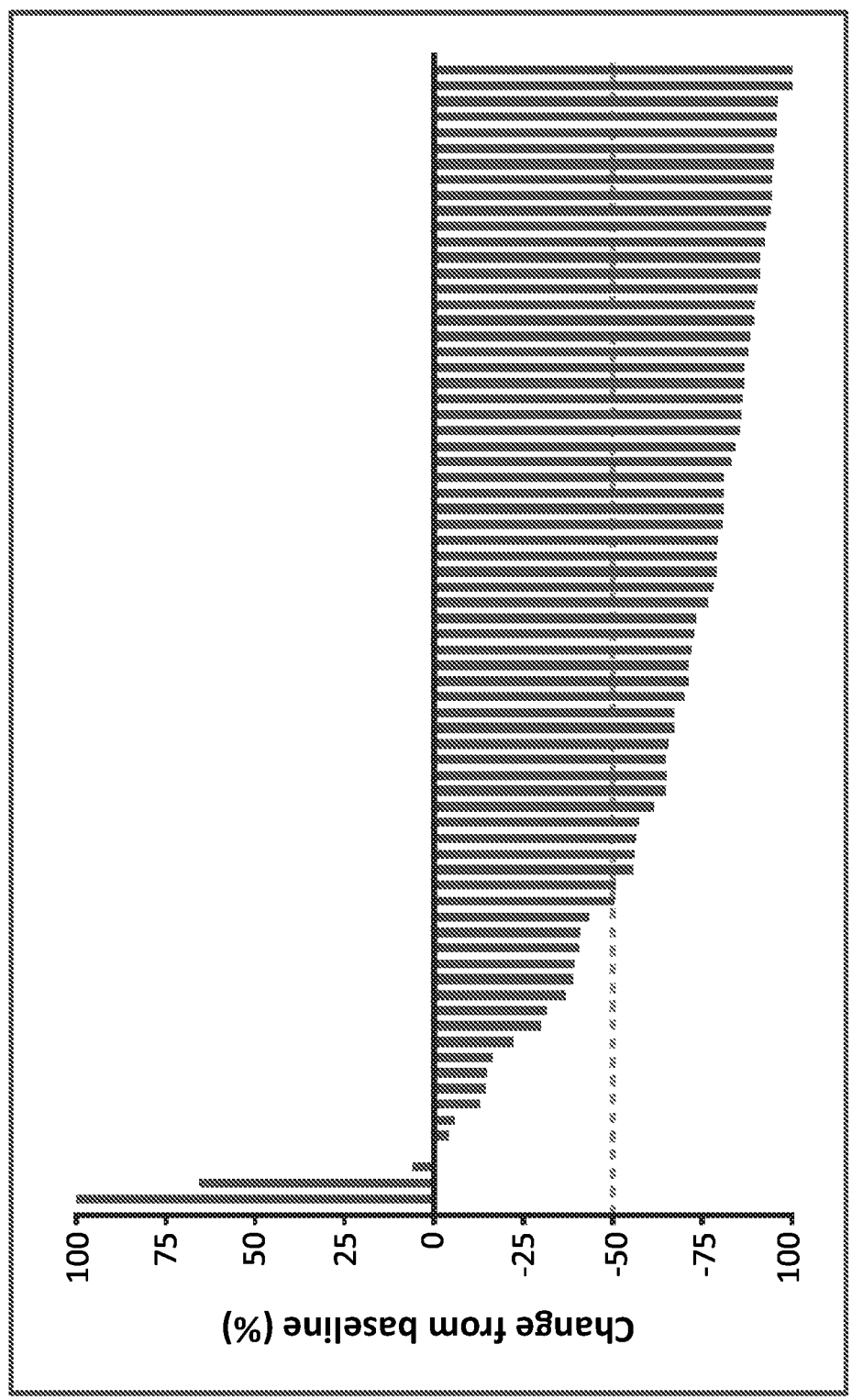

At time of analysis, 62% of the responders, as determined by the IRRC, continued to respond to nivolumab treatment. (See FIG. 2A). All but 1 responder had a reduction of ≥50% from baseline in tumor burden. (See FIG. 2B). This patient had a negative FDG-PET scan.

Figure 2C:
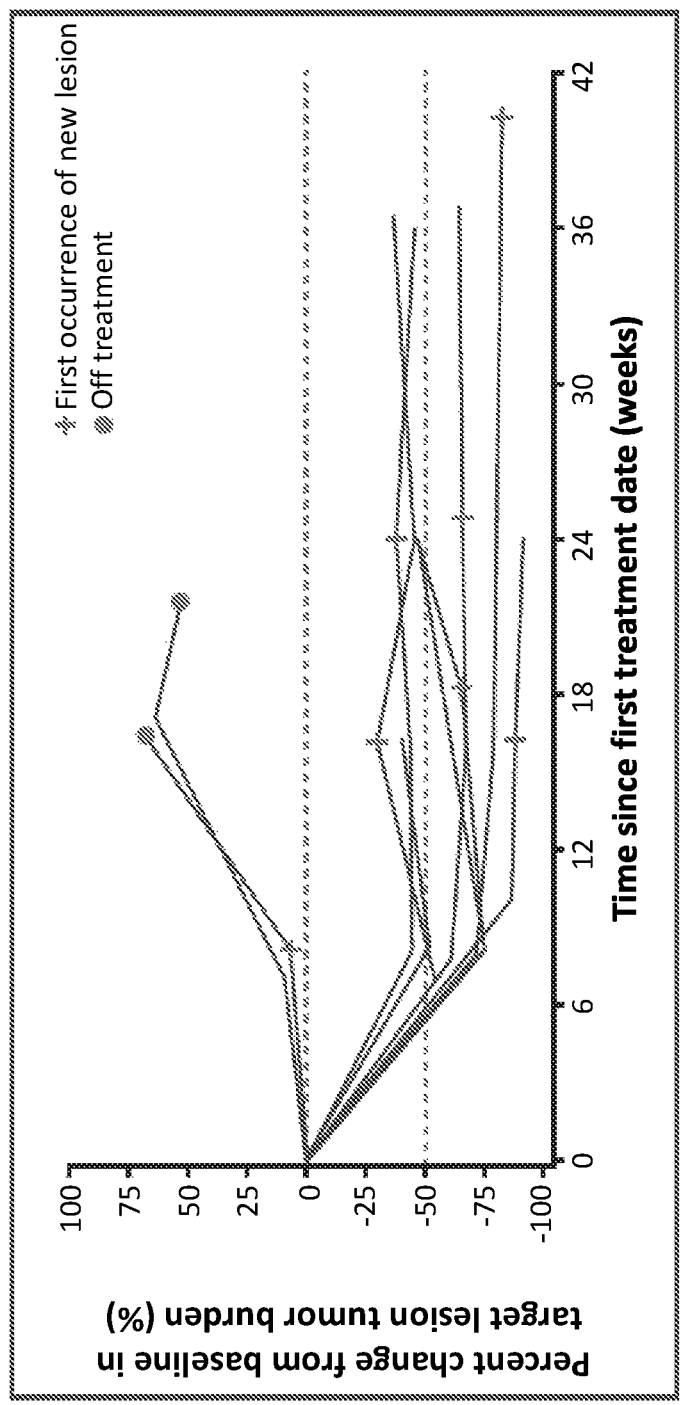

A total of 9 patients continued nivolumab beyond progression. As shown in FIG. 2C, 6 of the 9 patients maintained tumor reduction in target lesions, per investigator assessment.

Progression-Free Survival (PFS) and Overall Survival (OS)

Figure 3:
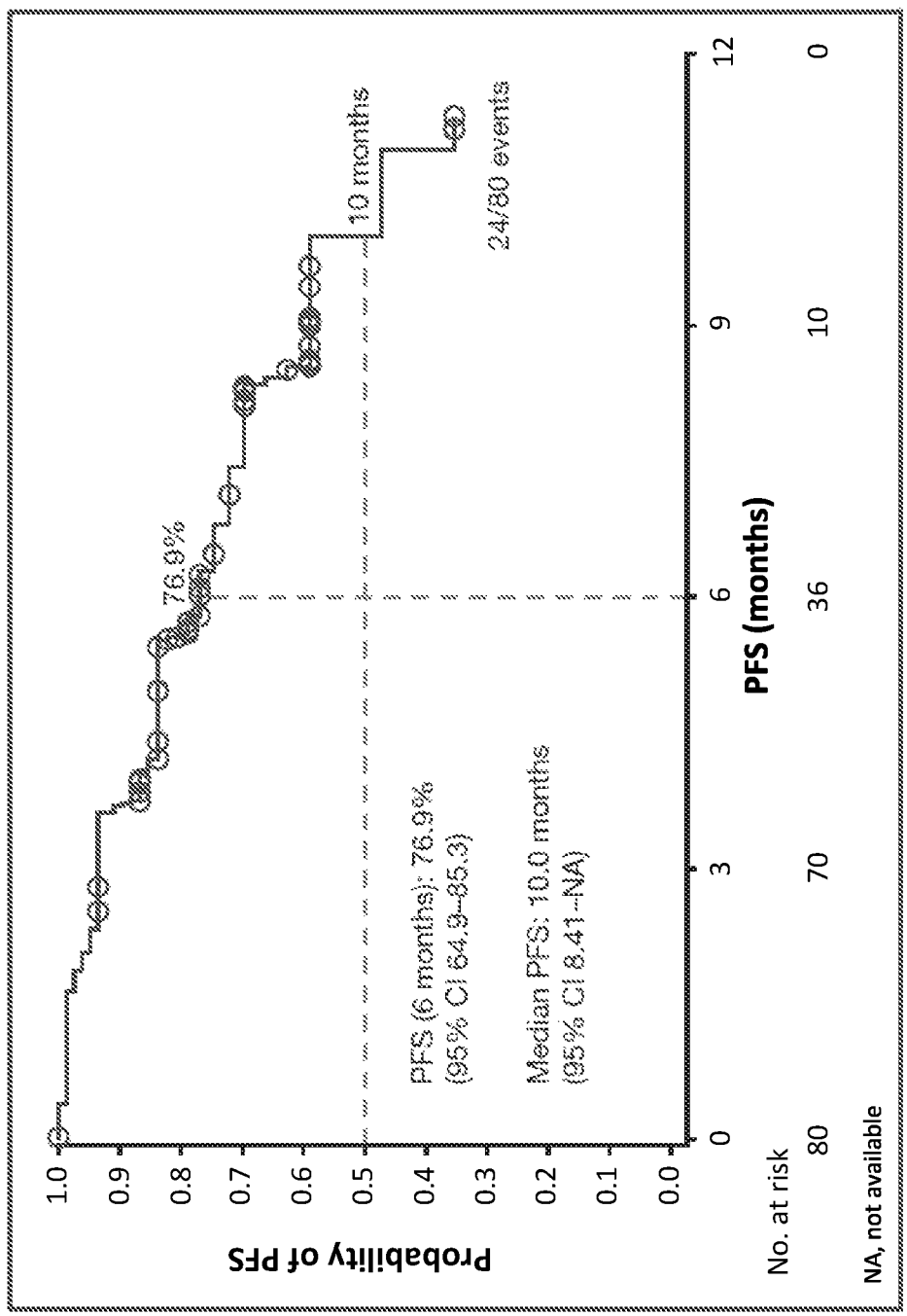
FIG. 3 shows the probability of progression free survival (PFS) over a course of 12 months in cHL patients treated with nivolumab. The median PFS was 10 months (95% CI 8.41 months—NA). The PFS at 6 months was 76.9% (95% CI 64.9%-85.3%) with an overall survival rate of 99% at 6 months.

As shown in FIG. 3, the median PFS among patients treated with nivolumab was 10 months. At 6 months, the PFS was 77% (95% CI 65%-85%) and the OS rate was 99% (95% CI 91%-100%).

Safety

All-cause adverse events (AEs) were reported in 79 of the 80 patients (99%), with serious AEs (grade 3-4) reported in 20 patients (25%). Drug-related AEs were reported in 72 patients. (See Table 4). Pneumonitis was reported in 2 patients (3%; grade 1/2 and grade 3) between the first dose and the 35 days after the last dose, which were considered drug-related.

All-cause AEs requiring discontinuation of nivolumab treatment included: autoimmune hepatitis (n=1), increased alanine aminotransferase and aspartate aminotransferase levels (n=1), and multi-organ failure (n=1). Three deaths have also been reported due to disease progression (n=1), an undetermined cause after lost follow-up (n=1), and multi-organ failure due to Epstein-Barr virus-positive T-cell lymphoma (n=1).

The most frequently reported AEs of special interest, regardless of causality, included skin (41%); gastrointestinal (26%); hypersensitivity/infusion-related reaction (21%); and endocrine (18%), hepatic (10%), renal (5%), and pulmonary (1%) events.

TABLE 4

Drug-related AEs in >10% of patients[a] (N = 80)

|  | Any grade | Grade 3-4 |
| --- | --- | --- |
| Patients with a drug-related event | 72 (90) | 20 (25) |
| Fatigue | 20 (25) | 0 |
| Infusion-related reaction | 16 (20) | 0 |
| Rash | 13 (16) | 1 (1) |
| Pyrexia | 11 (14) | 0 |
| Arthralgia | 11 (14) | 0 |
| Nausea | 10 (13) | 0 |

TABLE 4-continued

Drug-related AEs in >10% of patients[a] (N = 80)

|  | Any grade | Grade 3-4 |
|---|---|---|
| Diarrhea | 8 (10) | 0 |
| Pruritus | 8 (10) | 0 |

Data shown as n (%)
[a] AES occurring within 30 days of last dose

Quality of Life

Over time on treatment with nivolumab, the mean EQ-5D visual analog score increased. The EORTC QLQ-C30 also showed a trend towards improvement from baseline across functional, symptom, and global health scores.

Conclusions

In this registrational study in patients with cHL who had failed ASCT and brentuximab vedotin, nivolumab monotherapy resulted in the following observations: 1) 66.3% of patients had an objective response rate (ORR) per IRRC assessment; 2) preliminary durability of response was encouraging, with 62% of the patients continuing to respond at data cutoff (median duration of response of 7.8 months) and a median PFS of 10.0 months; and 3) acceptable safety profile with mostly grade 1 or 2 AEs and no new safety concerns versus solid tumors.

Example 2

A Phase 2 Study of a Nivolumab-Containing Regimen in Patients with Newly Diagnosed Classical Hodgkin Lymphoma Objectives The primary objective of this study is to assess overall safety and tolerability of nivolumab monotherapy followed by nivolumab in combination with AVD (doxorubicin, vinblastine, and dacarbazine) in newly diagnosed patients with advanced-stage cHL. This will be measured as patients who experienced ≥ graded 3-5 treatment-related AE between the first dose and 30 days after the last dose.

The secondary objectives of this study include: 1) safety and tolerability of nivolumab as monotherapy and in combination with AVD; 2) treatment discontinuation rate during monotherapy, in combination with AVD, and overall; and 3) clinical activity as measured by complete response (CR) rate, assessed by independent radiologic review committee using 2007 International Working Group criteria.

The exploratory objectives of this study include: 1) objective response rate, and 2) progression-free survival (PFS).

Study Design

This is a single-arm, open-label, phase 2 study assessing the safety and tolerability of nivolumab monotherapy followed by nivolumab in combination with AVD in newly diagnosed patients with advanced-stage cHL. The study is conducted in 8 countries in North America and the EU with a planned enrollment of 50 patients with newly diagnosed advanced-stage cHL.

As described in Table 5, the key inclusion criteria for enrollment in this study include: 1) newly diagnosed, previously untreated cHL (except corticosteroid use); 2) adults aged ≥18 years; 3) advanced-stage (IIB, III, and IV) disease; 4) presence of ≥1 lesion >15 mm diameter; and 5) ECOG performance status ≤1. The exclusion criteria are: 1) known CNS lymphoma; 2) known nodular lymphocyte-predominant HL; 3) active interstitial pneumonitis; 4) active or suspected autoimmune disease; and 5) HIV+ or hepatitis B/C.

TABLE 5

Key Inclusion/Exclusion Criteria

| Inclusion | Exclusion |
|---|---|
| Newly diagnosed, previously untreated cHL (except corticosteroid use) | Known CNS lymphoma |
| Adults aged ≥18 years | Known nodular lymphocyte-predominant HL |
| Advanced-stage (IIB, III, and IV) disease Stage IIB disease must have bulky disease or extranodal disease | Active interstitial pneumonitis |
| Presence of ≥1 lesion >15 mm diameter | Active or suspected autoimmune disease |
| ECOG performance status ≤1 | HIV+ or hepatitis B/C |

CNS = central nervous system

Figure 4:
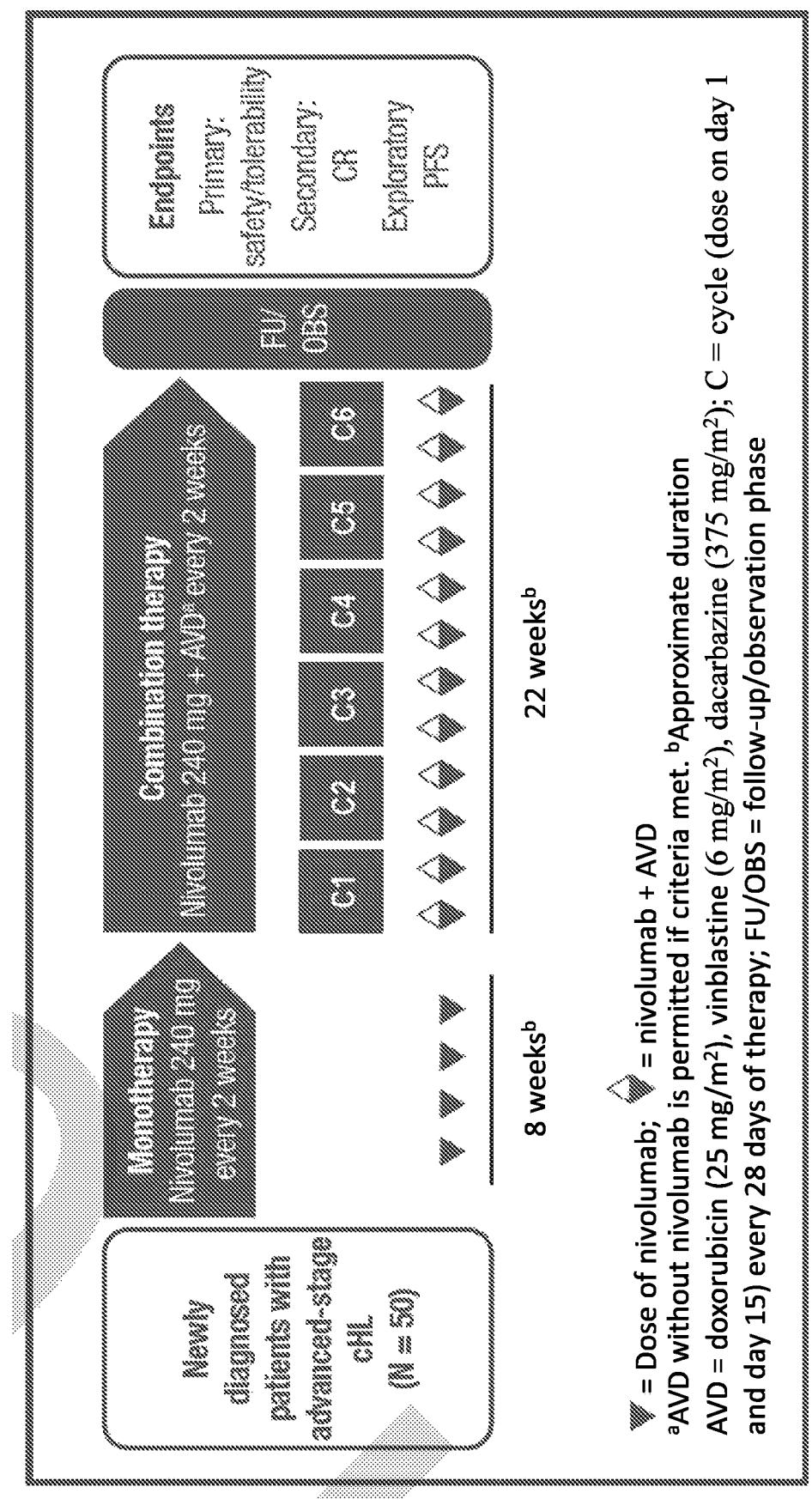
FIG. 4 shows a study design schematic for the single-arm, open-label, phase 2 study assessing the safety and tolerability of nivolumab monotherapy followed by nivolumab in combination with doxorubicin (25 mg/m2), vinblastine (6 mg/m2), dacarbazine (375 mg/m2) ("AVD") in newly diagnosed advanced-stage cHL. C means cycle (dose on day 1 and day 15) every 28 days of therapy. FU/OBS means follow-up and observation phase.

As shown in FIG. 4, patients meeting the above inclusion criteria first receive nivolumab alone (240 mg) every 2 weeks for 4 doses ("monotherapy phase"). Then, the patients receive nivolumab (240 mg) in combination with AVD every 2 weeks for 6 combo-cycles ("combination phase"). Patients are initially observed for a maximum of 2 years after last treatment ("observation phase"). If no relapse occurs during the observation phase, patients are followed for up to an additional 5 years for survival analysis.

What is claimed is:

1. A method of treating a subject afflicted with a tumor derived from a Hodgkin lymphoma, comprising administering to the subject an antibody or an antigen-binding portion thereof that binds specifically to a Programmed Death-1 receptor (PD-1), wherein the subject is previously untreated except with corticosteroid; and wherein the antibody or an antigen-binding portion thereof is administered (i) at a flat dose of about 240 mg every 2 weeks for 4 doses and then (ii) at a flat dose of about 240 mg about every 2 weeks in combination with doxorubicin, vinblastine, and dacarbazine.

2. The method of claim 1, wherein the subject is not administered bleomycin.

3. The method of claim 1, wherein the doxorubicin is administered at a dose of about 10 mg/m$^2$ to about 40 mg/m$^2$; the vinblastine is administered at a dose of about 0.1 mg/m$^2$ to about 10 mg/m$^2$; and/or the dacarbazine is administered at a dose of about 200 mg/m$^2$ to about 500 mg/m$^2$.

4. The method of claim 1, wherein the doxorubicin is administered at a dose of 25 mg/m$^2$, the vinblastine is administered at a dose of 6 mg/m$^2$, and the dacarbazine is administered at a dose of 375 mg/m$^2$ once about every 2 weeks.

5. The method of claim 1, wherein the anti-PD-1 antibody is nivolumab.

6. The method of claim 1, wherein the Hodgkin lymphoma has a genetic alteration at 9p24.1.

7. The method of claim 1, wherein the Hodgkin lymphoma expresses PD-L1 and/or PD-L2.

8. The method of claim 7, wherein at least 1% of tumor cells of Hodgkin lymphoma express the PD-L1 and/or PD-L2.

9. The method of claim 1, wherein the subject exhibits progression-free survival of at least about one month after the initial administration.

10. The method of claim 1, wherein the subject exhibits an overall survival of at least about five years after the initial administration.

11. The method of claim 1, wherein the anti-PD-1 antibody is pembrolizumab.

\* \* \* \* \*